United States Patent [19]

Petraitis

[11] Patent Number: 5,290,817
[45] Date of Patent: Mar. 1, 1994

[54] SUBSTITUTED 1-BENZYLINDANES AND THEIR USE AS INHIBITORS OF PHOSPHOLIPASE $A_2$

[75] Inventor: Joseph J. Petraitis, Glenmoore, Pa.

[73] Assignee: The Du Pont Merck Pharmaceutical Co., Wilmington, Del.

[21] Appl. No.: 895,688

[22] Filed: Jun. 9, 1992

[51] Int. Cl.$^5$ .................... A61K 31/11; C07C 47/52
[52] U.S. Cl. .................................. 514/700; 568/439
[58] Field of Search .................. 568/439; 514/700

[56] References Cited

U.S. PATENT DOCUMENTS 3,399,049 8/1968 Evans et al. .................. 568/439 X
3,904,691 9/1975 Carnmalm et al. ............. 568/439 X

OTHER PUBLICATIONS

Chemical Abstracts 111: 190105, 1989.
Chemical Abstracts 77: 151743, 1972.
Chemical Abstracts 71: 70392, 1968.
Chemical Abstracts 70: 3838, 1968.
Chemical Abstracts 68: 75556, 1968.

Primary Examiner—Marianne M. Cintins
Assistant Examiner—Catherine Scalzo
Attorney, Agent, or Firm—Gerald J. Boudreaux

[57] ABSTRACT

The invention relates to benzylindane phospholipase $A_2$ inhibitors, pharmaceutical compositions containing them, and methods of treating phospholipase $A_2$-mediated conditions in mammals by administration of a therapeutically effective amount of such a benzylindane phospholipase $A_2$ inhibitor including the representative example:

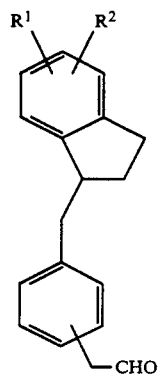

27 Claims, No Drawings

SUBSTITUTED 1-BENZYLINDANES AND THEIR USE AS INHIBITORS OF PHOSPHOLIPASE A₂

FIELD OF THE INVENTION

This invention relates to substituted 1-benzylindanes, pharmaceutical compositions containing them, and methods of using them. These compounds have shown activity as inhibitors of the enzyme phospholipase $A_2$.

BACKGROUND OF THE INVENTION

The important role of phospholipase $A_2$ in the biosynthesis of prostaglandins and leukotrienes indicates that inhibitors of phospholipase $A_2$ may be valuable therapeutic agents having wide applicability in inflammatory and/or allergic conditions in mammals. Although some currently available anti-inflammatory agents show activity against phospholipase $A_2$ or other enzymes of the "arachidonic acid cascade", there is a continuing need for safer and more effective drugs capable of treating inflammatory and/or allergic diseases.

The rationale for, and reports of, production of effective inhibitors of phospholipase $A_2$ as potential anti-inflammatory drugs have been outlined extensively in a recent review (see Wilkerson, *Drugs of the Future*, 15(2), 140 (1990).

In U.S. Pat. No. 4,371,543, issued Jun. 5, 1981 to G. C. Rovnyhak, there are disclosed bis-amide indene ketone compounds of the formula:

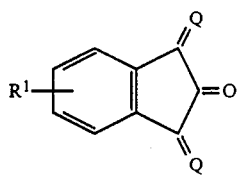

where Q is a group of the formula:

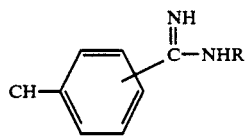

These compounds were claimed as anti-inflammatory agents.

German Patent 2,462,380, issued Dec. 20, 1973, discloses a process to produce an anti-inflammatory benzylidene indene acetic acid claimed in U.S. Pat. No. 3,654,349 of the formula:

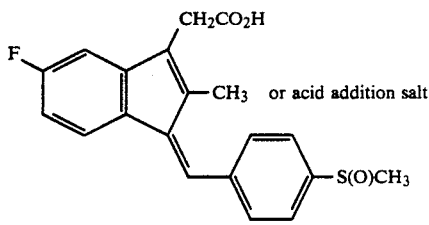

Also therein claimed as anti-inflammatory intermediates are compounds of the formula:

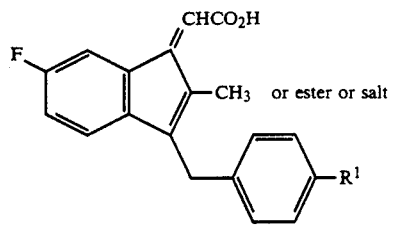

wherein $R^1$ is $SCH_3$ or $S(O)CH_3$.

U.S. Pat. No. 3,681,436, issued Aug. 1, 1972 to D. M. Lynch and J. W. Cole, discloses substituted 1-benzylindanes of the formula:

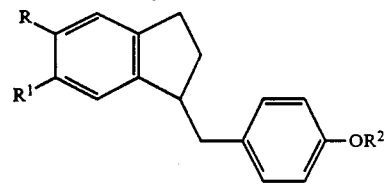

wherein R is OH, methoxy or acetoxy, $R^1$ is H or R and $R^2$ is H, methyl or acetyl. These compounds have been found to inhibit the metabolic function of female reproductive organs in warm-blooded animals.

U.S. Pat. No. 4,013,682, issued Mar. 22, 1977 to H. J. Panneman, discloses compounds of the formula:

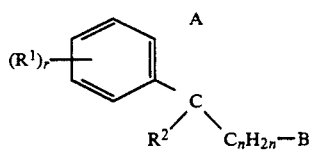

These compounds possess vasodilatory and antihypertensive properties.

U.S. Pat. No. 4,528,508, issued Jul. 9, 1985 to E. Plummer, disclosed indanes of the formula:

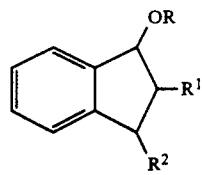

W. C. Ripka, W. J. Sipio, and W. G. Galbraith, in *Journal of Cellular Biochemistry*, 40, 279-286 (1989), describe a compound of the formula:

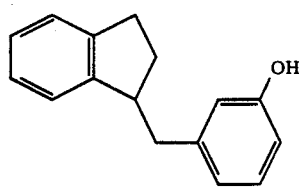

which is claimed to possess inhibitory activity against porcine pancreatic phospolipase $A_2$.

Phospholipase $A_2$ ($PLA_2$) acts to release arachidonic acid from phospholipids. Once released, arachidonic acid is rapidly metabolized by a variety of enzymes of the "arachidonic acid cascade." The products of the arachidonic acid cascade include prostaglandins, leukotrienes, and related compounds. These compounds exhibit a remarkably broad spectrum of biological activity, and inhibition of their biosynthesis is recognized as a valuable mechanism for production of anti-inflammatory effects.

Both prostaglandins and leukotrienes are believed to have important functions as mediators of inflammation and currently available drugs which inhibit their production are of significant therapeutic value in man and other mammals. Nonsteroidal anti-inflammatory agents such as the salicylates act as inhibitors of prostaglandin synthesis from arachidonic acid by inhibiting the cyclooxygenases. This inhibition of prostaglandin synthesis is believed to be the basis for many of the therapeutic effects of the aspirin-like drugs. The anti-inflammatory activity of the glucocorticosteroids, on the other hand, is believed to be at least partly due to their ability to induce the biosynthesis of a $PLA_2$ inhibitor protein, thereby diminishing the release of arachidonic acid from phospholipids. By decreasing concentrations of arachidonic acid, the substrate for the entire arachidonic acid cascade, production of leukotrienes as well as prostaglandins can be decreased.

Many diseases and conditions in man and other mammals have inflammatory and/or allergic components believed to be mediated by $PLA_2$, e.g., rheumatoid arthritis and other rheumatic disorders, various collagen diseases, dermatoses, psoriasis, hypersensitivity and immune reactions, bronchospastic diseases such as asthma, and disorders of platelet aggregation. Because the compounds of this invention have shown activity as $PLA_2$ inhibitors, valuable pharmacological activity in these and other diseases or conditions mediated by the various products of the arachidonic acid cascade is to be expected.

SUMMARY OF THE INVENTION

This invention relates to substituted 1-benzylindanes, which are phospholipase $A_2$ inhibitors, pharmaceutical compositions containing them, and methods of using them to treat inflammation in mammals. These compounds have the general formula (I):

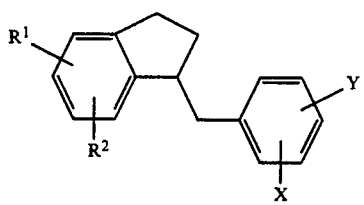

or a pharmaceutically acceptable salt thereof; wherein:
$R^1$ is H, halo, $C_1$-$C_4$ alkyl, $OR^3$ or $CO_2R^4$;
$R^2$ is H or when $R^1$ is 6—$OR^3$, then $R^2$ may be 5—$CO_2R^4$;
X is $COR^3$, $CO_2R^4$, CN, $NHR^4$, $COCH_2R^5$, CHO, $CH_2CHO$, $CH_2CH_2OH$, $CH_2OH$, $CH_2NH_2$, $CF_2CHO$, $CF_2CH_2OH$, $COCF_3$, $C_1$-$C_4$, alkyl, halo,

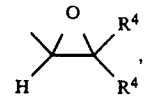

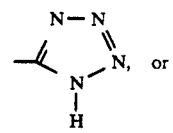

Y is H, or when X is —CHO, then Y may be ortho —OH relative to —CHO;
$R^3$ is $C_1$-$C_4$ alkyl;
$R^4$ is H or $C_1$-$C_4$ alkyl; and
$R^5$ is Cl, Br, or $N_3$; provided that:
(a) when X is $COCH_2R_5$, then neither $R^1$ nor $R^2$ is $CO_2H$;
(b) when $R^1$ is $OR^3$, then X is not $OR^3$;
(c) when X is CHO and Y is OH, then $R^1$ is not $OR^3$;
(d) neither $R^1$ nor $R^2$, except when H, resides at the 7-position;
(e) when X is $CF_2CHO$ or $CF_2CH_2OH$, then neither $R^1$ nor $R^2$ is $CO_2R^4$;
(f) when $R^1$ or $R^2$ is $CO_2R^4$ and X is $CO_2R^4$, then $R^4$ is the same in $R^1$ or $R^2$ and in X;
(g) when $R^1$ is 6—$OR^3$ and $R^2$ is 5—$CO_2R^4$, then X may be only $CH_2CHO$ or formula II; and
(h) when X is $B(OH)_2$ or

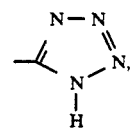

then neither $R^1$ nor R2 is $CO_2R^4$.

Preferred compounds are those of formula (I): wherein:
X is $COR^3$, $OR^3$, $CO_2R^4$, $COCH_2R^5$, CN, CHO, $CH_2CHO$, or

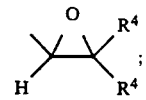

Y is H, but if X is CHO, then Y may be OH ortho to CHO;
$R^3$ is $C_{1-4}$ alkyl;
$R^4$ is H, or $C_{1-4}$ alkyl; and
$R^5$ is Cl, Br, or $N_3$.

More preferred compounds are the preferred compounds in which
Y is $COCH_2Br$,

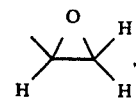

$CH_2CHO$, or CHO; and
Y is H, and if X is —CHO, then Y may be OH ortho to CHO.

Specifically preferred compounds are:
(1) 3-(2',3'-dihydroinden-1'-ylmethyl)-alpha-bromoacetophenone;
(2) 3-(2',3'-dihydroinden-1'-ylmethyl)-oxiranylbenzene;
(3) 4-(2',3'-dihydroinden-1'-ylmethyl)-oxiranylbenzene;
(4) 4-(2',3'-dihydroinden-1'-ylmethyl)-phenylacetaldehyde;
(5) 3-(2',3'-dihydroinden-1'-ylmethyl)phenylacetaldehyde;
(6) 3-(2',3'-dihydroinden-1'-ylmethyl)-2-hydroxybenzaldehyde.

DETAILED DESCRIPTION OF THE INVENTION

The compounds of this invention have demonstrated pharmacological activity as inhibitors of the enzyme phospholipase $A_2$ ($PLA_2$).

SYNTHESIS

There are many ways well known to those skilled in the art of organic chemistry to prepare the compounds of the present invention. Some of these are detailed below.

The compounds of formula (I), in which Y is hydrogen, CN, $NO_2$, or alkyl of 1–4 carbon atoms, may be prepared from phosphonium salts of formula (III) by treatment with a base, for example potassium hydride, using a method similar to that described by James, Pattendon, and Barlow, *J. Chem. Soc., Perkin I*, 1466 (1976), followed by addition of an 1-indanone of formula (IV). The reaction may be carried out in a solvent, such as dry tetrahydrofuran, between room temperature and reflux under an atmosphere of nitrogen. Aqueous workup followed by chromatographic purification provides compounds of formula (V). Hydrogenation of (V) in ethanol at room temperature and 50 psi in the presence of a catalyst, for example 10% palladium-on-carbon, provides compounds of formula (VI). This method is shown in Scheme 1.

Scheme 1

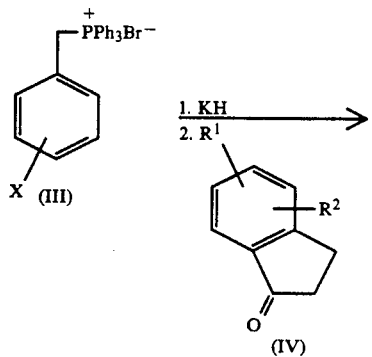

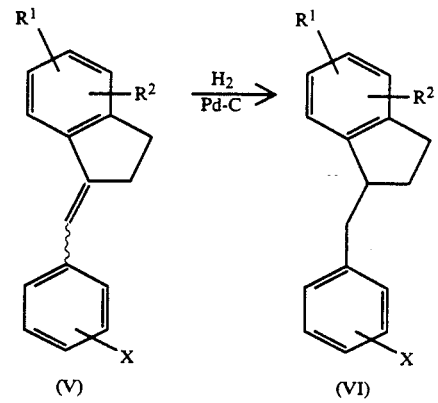

X is $OR^3$, CN, $NO_2$, or alkyl of 1–4 carbon atoms

The compounds of formula (IV), in which $R^1$ is $OR^3$, F, or alkyl of 1–4 carbon atoms and $R^2$ is hydrogen, if not commercially available, could be prepared as described by Nakada, Muramatsu, Asai, Ohno, and Yura, *Agric. Biol. Chem.*, 42 (7), 1357–1373 (1978).

The compounds of formula (IV), in which $R^1$ is 4—$CO_2H$ or 6—$CO_2H$ and $R^2$ is hydrogen, could be prepared as described by Exner and Friedl, *Collect. Czech. Chem. Commun.*, 43 (12), 3227 (1978).

The compounds of formula (IV), in which $R^1$ is 5—$CO_2H$ and $R^2$ is hydrogen, could be prepared as described by Allinger and Jones, *J. Org. Chem.*, 27, 70 (1962).

The compounds of formula (IV), in which $R^1$ is $CO_2R^3$ and $R^2$ is hydrogen, could be prepared from compounds of the formula (VII). Thus, treatment of (VII) with a diazoalkane, as described in March, "Advanced Organic Chemistry: Reactions, Mechanisms, and Structure," p.324, McGraw-Hill, New York, 1968, could provide compounds of formula (VIII). This method is illustrated in Scheme 2.

Scheme 2

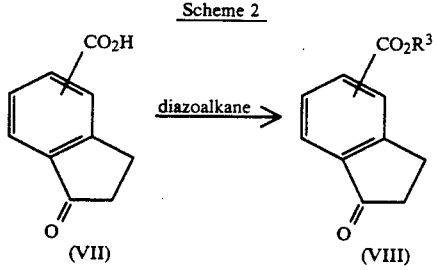

The compounds of Formula (I), in which $R^1$ and $R^2$ are hydrogen and and X is $OR^3$, CN, or alkyl of 1–4 carbon atoms, may also be prepared from indene by treatment with a base, for example n-butyllithium, followed by addition of a substituted benzyl bromide of formula (IX). The reaction may be carried out in a solvent, for example dry tetrahydrofuran, cooled with a dry ice/acetone bath under an atmosphere of nitrogen. Aqueous workup and chromatographic purification provides a crude mixture, which may be subjected to hydrogenation in ethanol at 50 psi in the presence of 10% palladium-on-carbon. Chromatographic purification provides compounds of the formula (X). This method is illustrated in Scheme 3.

Scheme 3

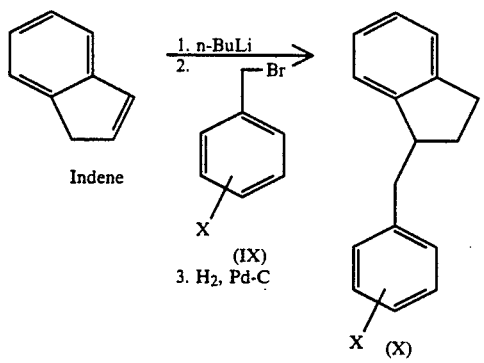

The compounds of formula (IX), in which X is OR³, CN, NO₂, or alkyl of 1–4 carbon atoms, if not commercially available, could be prepared from compounds of formula (XI). Thus, treatment of (XI) with carbon tetrabromide and triphenylphosphine, in methylene chloride between room temperature and −78° C., could provide compounds of formula (IX). The method is similar to that described by Hooz and Giliani, *Can. J. Chem.*, 46, 86 (1968). The method is illustrated in Scheme 4. The compounds of formula (III) may be prepared from compounds of formula (IX). Thus, treatment of (IX) with triphenylphosphine in a solvent, such as dry tetrahydrofuran, provides compounds of formula (III). The method is similar to that described by James, Pattendon, and Barlow, *J. Chem. Soc., Perkin I*, 1466 (1976). The method is illustrated in Scheme 5.

Scheme 4

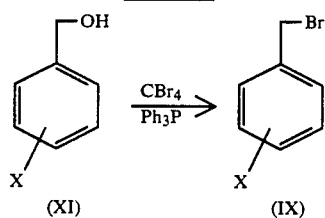

Scheme 5

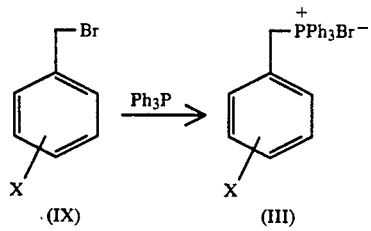

The compounds of formula (I), in which neither R¹ nor R² is CO₂R³, X is CHO and Y is hydrogen, may be prepared from compounds of formula (XII) by treatment with diisobutylaluminum hydride, using a method described by Miller, Biss, and Schwartzman, *J. Org. Chem.*, 24, 627 (1959). The reaction is carried out in toluene and cooled with a dry ice/acetone bath under an atmosphere of nitrogen. The reaction is allowed to warm to room temperature before quenching with dilute acetic acid. Aqueous workup, followed by chromatographic purification, provides compounds of formula (XIII). It is illustrated in Scheme 6.

Scheme 6

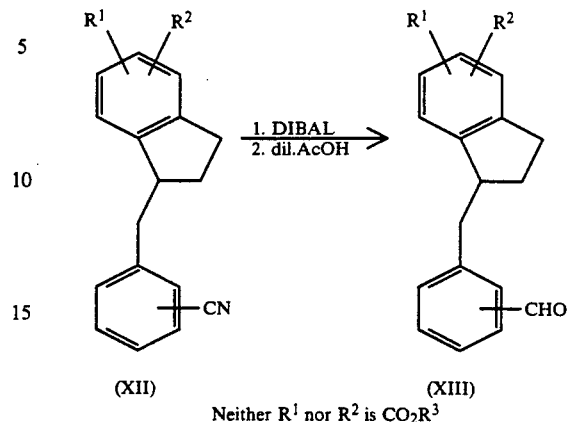

Neither R¹ nor R² is CO₂R³

The compounds of formula (I), in which R¹ or R² is CO₂R³, X is CHO and Y is hydrogen, could be prepared from compounds of formula (XIV), in which R² is not CO₂R³. Thus, treatment with a base, for example potassium carbonate, in the presence of a C₁-C₄ alkyl iodide, similar to that described in March, "Advanced Organic Chemistry: Reactions, Mechanisms, and Structure," p.323, McGraw-Hill, Inc., New York, 1968, in dry acetone between room temperature and reflux under an atmosphere of nitrogen, could provide compounds of formula (XV). The method is illustrated in Scheme 7.

Scheme 7

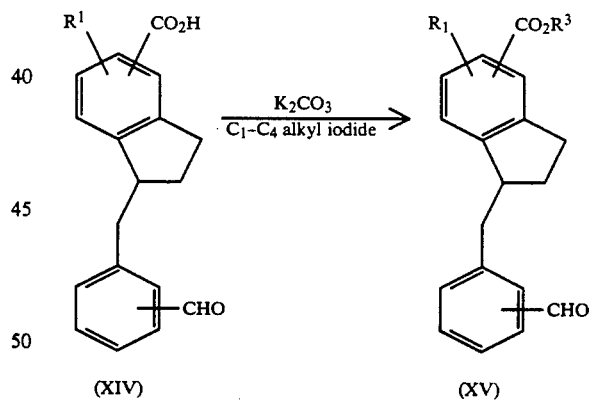

The compounds of formula (I), in which neither R¹ nor R² is CO₂R³ and X is COR³, may be prepared from compounds of formula (XII) by treatment with a C₁-C₄ alkylmagnesium chloride, using a method described in March, "Advanced Organic Chemistry: Reactions, Mechanisms, and Structure," p.691, McGraw-Hill, New York, 1968. The reaction may be carried out in a solvent, for example dry tetrahydrofuran, between room temperature and reflux. The mixture may be quenched with dilute hydrochloric acid followed by aqueous workup. Chromatographic purification provides compounds of formula (XVI). The method is illustrated in Scheme 8.

Scheme 8

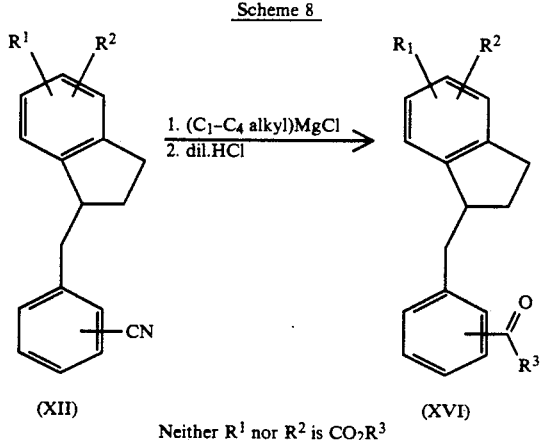

Neither $R^1$ nor $R^2$ is $CO_2R^3$

Alternatively, the compounds of formula (XVI) may be prepared from compounds of formula (V), in which neither $R^1$ nor $R^2$ is $CO_2R^3$ and R is CN (i.e. formula (XVII)), by treatment with a $C_1$-$C_4$ alkylmagnesium chloride, similar to that described for Scheme 8. The reaction may be carried out in a solvent, for example dry tetrahydrofuran, between room temperature and reflux. Quenching with dilute hydrochloric acid, followed by aqueous workup and chromatographic purification, provides compounds of formula (XVIII). Hydrogenation of (XVIII) in ethanol in the presence of 10% palladium-on-carbon at 50 psi, after chromatographic purification, provides compounds of formula (XVI). This process is illustrated in Scheme 9.

Scheme 9

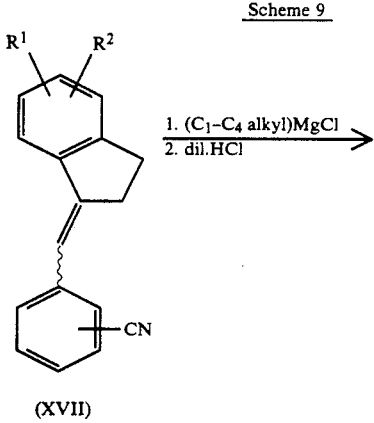

(XVII)

-continued
Scheme 9
Neither $R^1$ nor $R^2$ is $CO_2R^3$

The compounds of formula (I), in which $R^1$ or $R^2$ is $CO_2R^3$ and X is $COR^3$, could be prepared from compounds of formula (XIX) by treatment with a base, for example potassium carbonate, in the presence of a $C_1$-$C_4$ alkyl iodide, using the method described in Scheme 7. The reaction could be carried out in dry acetone between room temperature and reflux under an atmosphere of nitrogen. Aqueous workup could provide compounds of formula (XX). This is illustrated in Scheme 10.

Scheme 10

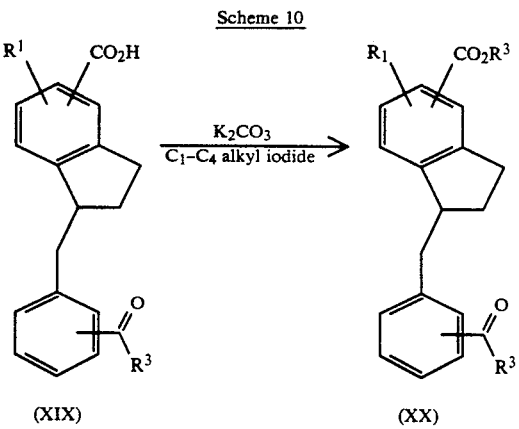

The compounds of formula (I), in which neither $R^1$ nor $R^2$ is $CO_2R^3$ and X is $CO_2H$, may be prepared from compounds of formula (XVII) by treatment with sodium hydroxide, using a method described in March, "Advanced Organic Chemistry: Reactions, Mechanisms, and Structure," p.660, McGraw-Hill, New York, 1968. The reaction may be carried out in aqueous ethanol between room temperature and reflux under an atmosphere of nitrogen. Acidification, followed by aqueous workup and chromatographic purification, leads to formation of compounds of the Formula (XXI). Hydrogenation of (XXI) in ethanol at 50 psi in the presence of 10% palladium-on-carbon leads to formation of compounds of formula (XXII). This is illustrated in Scheme 11.

Scheme 11

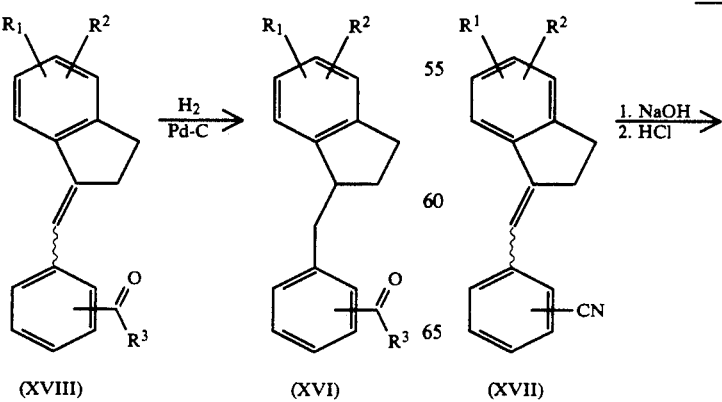

-continued

Scheme 11

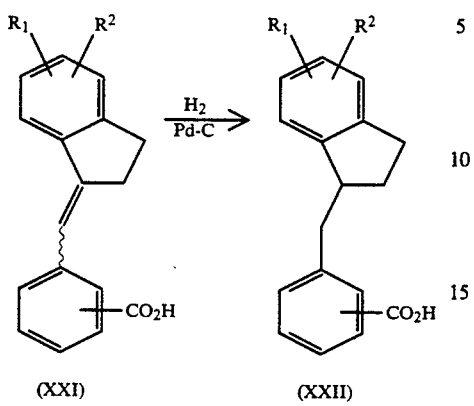

Neither R¹ nor R² is CO₂R³

The compounds of formula (I), in which X is CO₂R³, could be prepared from compounds of formula (XXII) by treatment with a base, for example potassium carbonate, in the presence of a $C_1$–$C_4$ alkyl iodide, using a method described for Scheme 7. The reaction could be carried out in dry acetone between room temperature and reflux under an atmosphere of nitrogen. Aqueous workup could provide compounds of formula (XXIII). This is illustrated in Scheme 12.

Scheme 13

Neither R¹ nor R² is CO₂R³

The compounds of formula (I), in which R¹ or R² is CO₂R³ and X is OH, could be prepared from compounds of formula (XXV) by treatment with a base, for example potassium carbonate, in the presence of a $C_1$–$C_4$ alkyl iodide, using a method described for Scheme 7. The reaction could be carried out in dry acetone between room temperature and reflux under an atmosphere of nitrogen. Aqueous workup could provide compounds of the Formula (XXVI). This is illustrated in Scheme 14.

Scheme 12

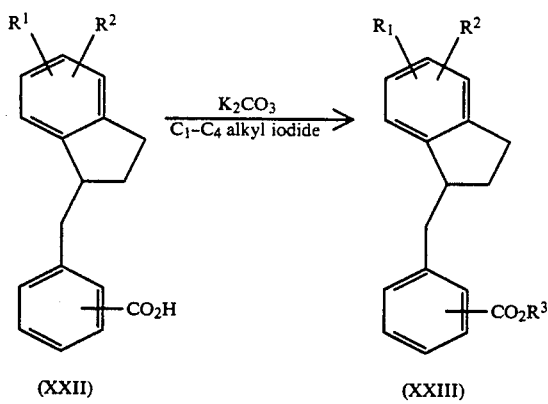

The compounds of formula (I), in which X is OH and neither R¹ nor R² is CO₂R³, could be prepared from compounds of formula (XIII) through a Baeyer-Villiger reaction as described in House, "Modern Synthetic Reactions," p.328, W. A. Benjamin, Inc., New York, 1965. Thus, treatment of (XIII) with hydrogen peroxide and water could lead to compounds of formula (XXIV). This is illustrated in Scheme 13.

Scheme 14

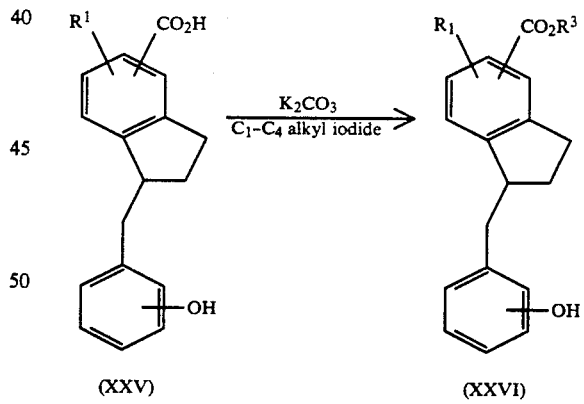

Compounds of formula (XXIV) may also be prepared from compounds of formula (XXVII) upon treatment with boron tribromide, using a method described in Manson and Musgrave, J. Chem. So., 1011 (1963). The reaction may be carried out in methylene chloride between −78° C. and room temperature under an atmosphere of nitrogen. Aqueous workup and chromatographic purification provides compounds of the Formula (XXIV).

Scheme 15

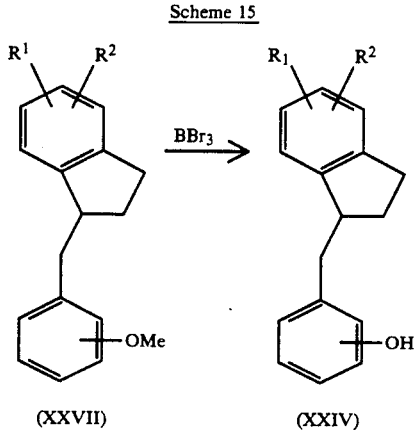

(XXVII) → (XXIV)

Scheme 17

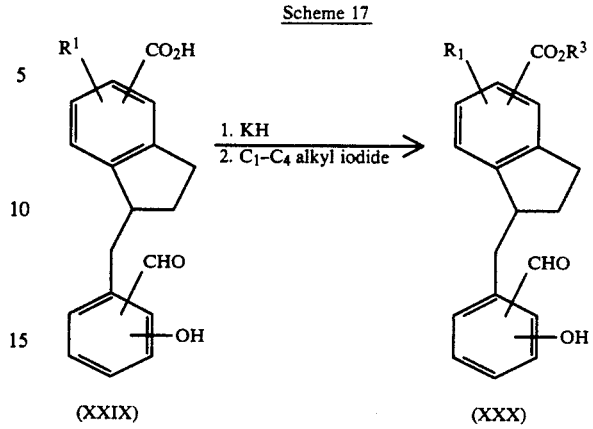

(XXIX) → (XXX)

The compounds of formula (I), in which neither $R^1$ nor $R^2$ is $CO_2R^3$ or CHO and Y is ortho-hydroxy, may be prepared from compounds of formula (XXIV) by treatment with chloroform in the presence of sodium hydroxide, using a method described in March, "Advanced Organic Chemistry: Reactions, Mechanisms, and Structure," p.419, McGraw-Hill, Inc., New York, 1968. Acidification, followed by aqueous workup and chromatographic purification, provides compounds of formula (XXVIII). This is illustrated in Scheme 15.

Scheme 15

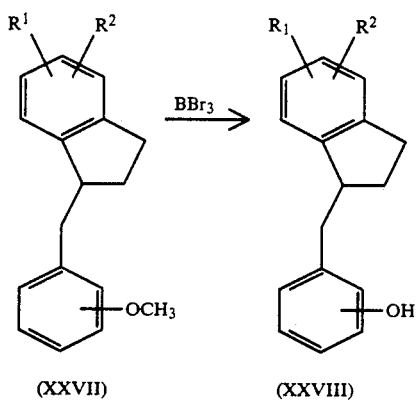

(XXVII) (XXVIII)

The compounds of formula (I), in which either $R^1$ or $R^2$ is $CO_2R^3$, or CHO and Y is ortho-hydroxy, could be prepared from compounds of formula (XXIX) by treatment with one equivalent of a base, for example potassium hydride, followed by addition of a $C_1$-$C_4$ alkyl iodide, similar to the conversion of (XIV) to (XV) in Scheme 7. The reaction could be carried out in a solvent, for example dry tetrahydrofuran, between room temperature and reflux. Aqueous workup could provide compounds of the Formula (XXX). This is illustrated in Scheme 17.

The compounds of formula (I), in which X is $NHR^4$, could be prepared from compounds of formula (XXXI). Thus, treatment of (XXXI) with a base, for example potassium hydride, followed by addition of a compound of formula (IV), could give rise to compounds of formula (XXXII). The reaction could be carried out analogous to the conversion of (III) to (V) in Scheme 1. Hydrogenation of (XXXII), under conditions analogous to the conversion of (V) to (VI) in Scheme 1, could give rise to compounds of formula (XXXIII). Treatment of (XXXIII) with a $C_1$-$C_4$ alkaldehyde in the presence of sodium cyanoborohydride, as reviewed in Aldrichimica Acta, 8(1), 3 (1975) and Ibid., 12(2), 34 (1979), could provide compounds of formula (XXXIV). This is illustrated in Scheme 18.

Scheme 18

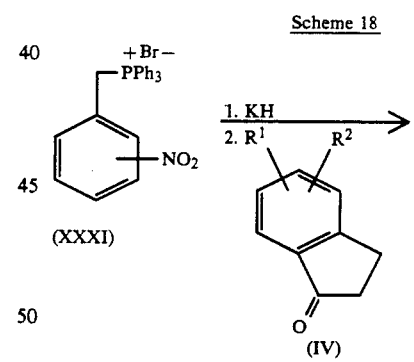

-continued
Scheme 18

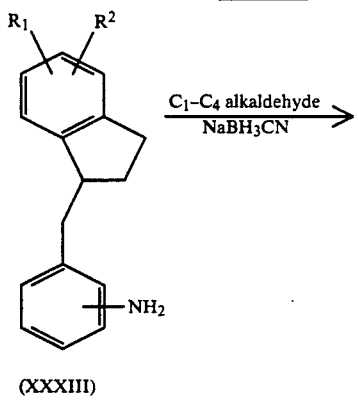 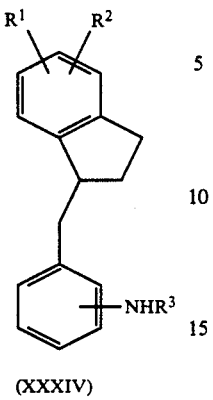

(XXXIII)  (XXXIV)

The compounds of formula (I), in which X is COCH$_2$Cl, could be prepared from compounds of formula (XXXV) in which neither R$^1$ nor R$^2$ is CO$_2$H. Thus, conversion of (XXXV) to (XXXVI) by treatment with thionyl chloride, followed by addition of one equivalent of diazomethane, as described by Clibbens and Nierenstein, *J. Chem. Soc.*, 107, 1491 (1915), could provide compounds of formula (XXXVIII). This is illustrated in Scheme 19.

Scheme 19

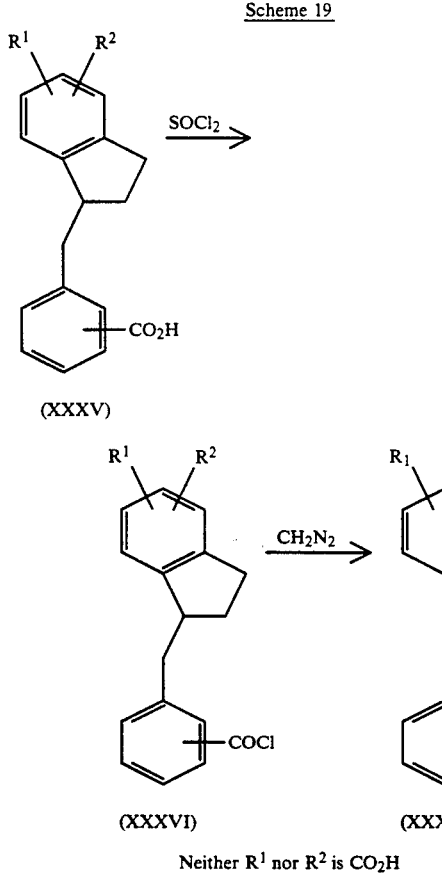

(XXXV)

(XXXVI)  (XXXVII)

Neither R$^1$ nor R$^2$ is CO$_2$H

The compounds of formula (I), in which X is COCH$_2$Br, may be prepared from compounds of formula (XXXVIII), in which neither R$^1$ nor R$^2$ is CO$_2$H. Thus, treatment of (XXXVIII) with bromine in acetic acid, at room temperature under an atmosphere of nitrogen, provides, after aqueous workup and chromatographic purification, compounds of formula (XXXIX). The method is shown in Scheme 20.

Scheme 20

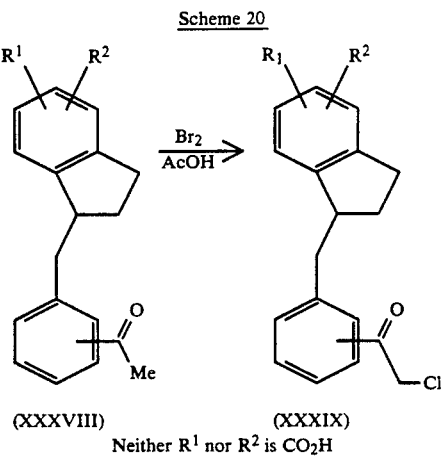

(XXXVIII)  (XXXIX)

Neither R$^1$ nor R$^2$ is CO$_2$H

The compounds of formula (I), in which X is COCH$_2$N$_3$, may be prepared from compounds of formula (XXXIX), in which neither R$^1$ nor R$^2$ is CO$_2$H, by treatment of (XXXIX) with sodium azide in aqueous methanol, using a method similar to that described by Henkel and Weygand, *Ber.*, 76, 812 (1943). The reaction may be carried out under an atmosphere of nitrogen with heating on a steam bath. Aqueous workup and chromatographic purification provides compounds of formula (XL). The method is shown in Scheme 21.

Scheme 21

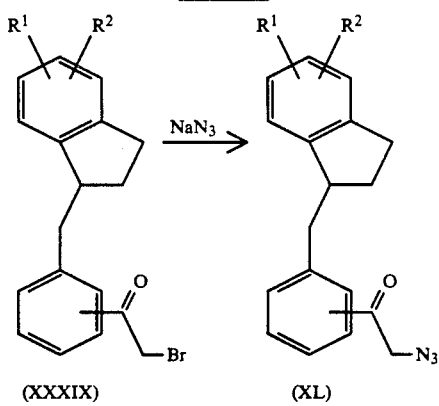

(XXXIX)  (XL)

The compounds of formula (I), in which X is CH$_2$CHO, may be prepared from compounds of formula (XLI). Thus, treatment of (XLI) with the product derived from the treatment of (methoxymethyl) triphenylphosphonium chloride with a base, for example potassium hydride, gives rise to a crude product upon aqueous workup and chromatographic separation. Treatment of this crude product with dilute acid, for example hydrochloric acid, provides, after aqueous workup and chromatographic purification, compounds of formula (XLII). The reaction is analogous to that described by Danishefsky, Nagasawa, and Wang, *J. Org. Chem.* 40, 1989 (1975). The method is shown in Scheme 22.

Scheme 22

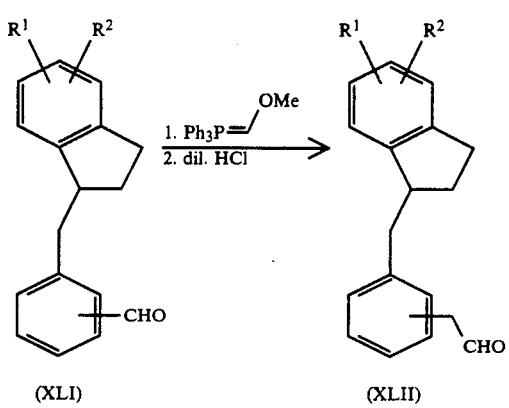

The compounds of formula (I), in which X is CH₂CH₂OH, could be prepared from compounds of formula (XLII) by treatment with sodium borohydride as described in March, "Advanced Organic Chemistry: Reactions, Mechanisms, and Structure," pp.678–681, McGraw-Hill, Inc., New York, 1968. Thus, compounds of formula (XLIII) could be prepared after aqueous workup and chromatographic purification. The method is shown in Scheme 23.

Scheme 23

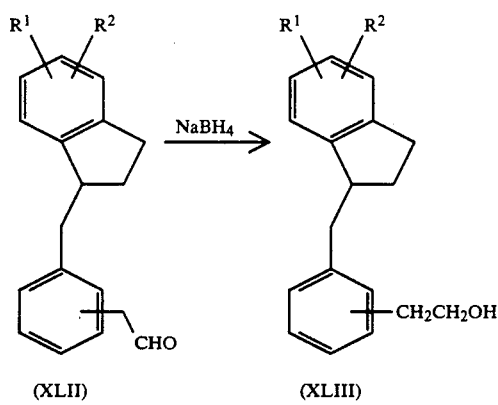

The compounds of formula (I), in which X is CH₂OH, could be prepared from compounds of formula (XLI). Thus, treatment of (XLI) with sodium borohydride, analogous to the conversion of (XLII) to (XLIII) in Scheme 23, could provide, after aqueous workup and chromatographic purification, compounds of formula (XLIV). The method is shown in Scheme 24.

Scheme 24

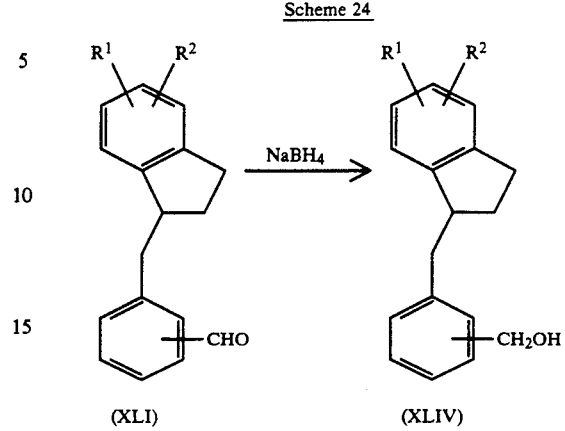

The compounds of formula (I), in which neither R¹ nor R² is CO₂R⁴ and X is CH₂OH, may be prepared from compounds of formula (XLV), in which neither R¹ nor R² is CO₂R⁴. Thus, treatment of (XLV) with lithium aluminum hydride, similar to that described in March, "Advanced Organic Chemistry: Reactions, Mechanisms, and Structure," p.678, McGraw-Hill, New York, 1968, could provide compounds of formula (XLVI). This method is shown in Scheme 25.

Scheme 25

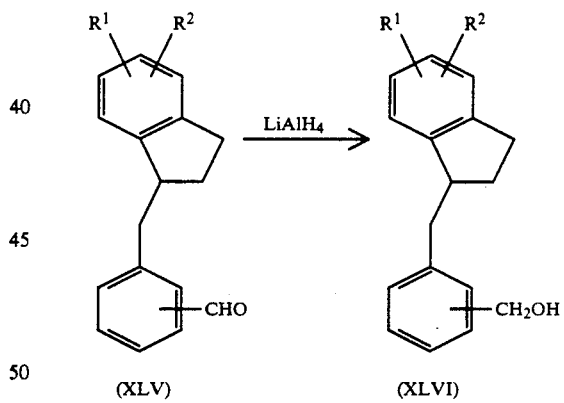

Neither R¹ nor R² is CO₂R⁴

The compounds of formula (I), in which neither R¹ nor R² is CO₂R⁴ and X is CH₂NH₂, may be prepared from compounds of formula (XLVII). Thus, treatment of (XLVII) with lithium aluminum hydride, in a manner similar to that described in March, "Advanced Organic Chemistry: Reactions, Mechanisms, and Structure," p.683, McGraw-Hill, New York, 1968, provides, after aqueous workup and chromatographic purification, compounds of formula (XLVIII). This is shown in Scheme 26.

Scheme 26

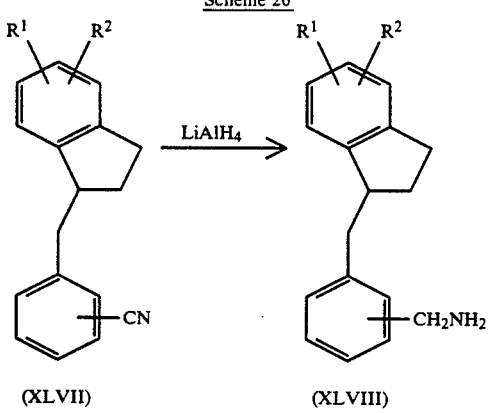

Neither $R^1$ nor $R^2$ is $CO_2R^4$

The compounds of formula (I), in which $R^1$ or $R^2$ is $CO_2H$ and X is $CH_2NH_2$, could be prepared from compounds of formula (XLIX). Thus, treatment of (XLIX) with lithium aluminum hydride, as described in Scheme 26, could provide, after aqueous workup and chromatographic purification, compounds of formula (L). Treatment of (L) with pyridinium dichromate, as described by Corey and Schmidt, *Tetrahedron Lett.*, 399 (1979), could provide, after aqueous workup and chromatographic purification, compounds of formula (LI). This is shown in Scheme 27.

Scheme 27

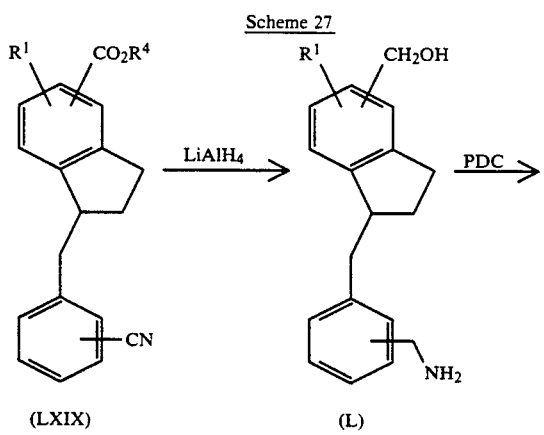

The compounds of formula (I), in which $R^1$ or $R^2$ is $CO_2R^3$ and X is $CH_2NH_2$, could be prepared from compounds of formula (LI). Thus, treatment of (LI) with a $C_1$–$C_4$ diazoalkane, similar to that described in Scheme 2, could provide, after aqueous workup and chromatographic purification, compounds of formula (LII). This is illustrated in Scheme 28.

Scheme 28

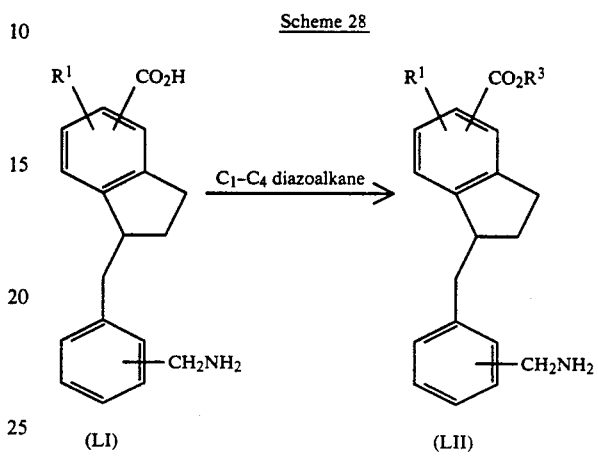

The compounds of formula (I), in which X is of formula (II), wherein one $R^4$ is hydrogen and the other $R^4$ is $C_1$–$C_4$ alkyl or hydrogen, may be prepared from compounds of formula (LIII), in a manner similar to that described by Corey and Chaykovsky, *J. Am. Chem. Soc.*, 87 (6), 1353 (1965). Thus, treatment of (LIII) with a base, for example potassium hydride in dry dimethylsulfoxide, followed by addition of a compound of the Formula (XLI), provides compounds of formula (LIV). This is shown in Scheme 29.

Scheme 29

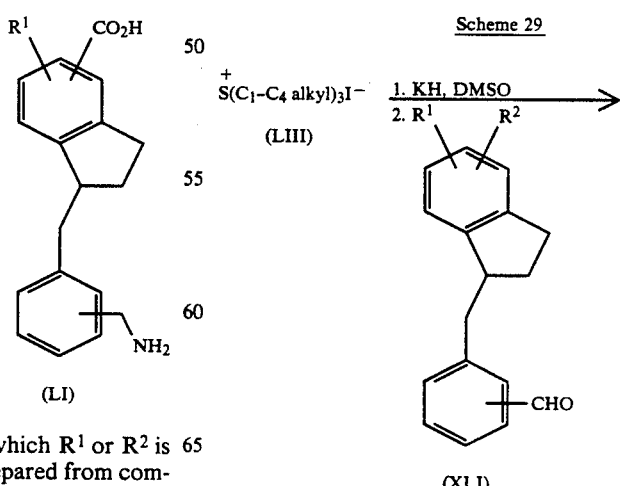

-continued
Scheme 29

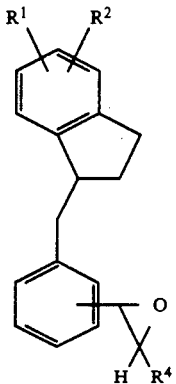

(LIV)

The compounds of the formula (I), in which X is of formula (II), wherein $R^4$ is $C_1$-$C_4$ alkyl, could be prepared from compounds of formula (LV), similar to the preparation of compounds of formula (LIV) in Scheme 29. Thus, treatment of (LV) with base, for example potassium hydride in dry dimethylsulfoxide, followed by addition of a compound of formula (XLI), could provide compounds of formula (LVI). This is shown in Scheme 30.

Scheme 30

$Ph_2SCH(C_1$-$C_4$ alkyl$)_2I^-$
(LV)

$\xrightarrow{\text{1. KH, DMSO} \atop \text{2. } R^1, R^2}$

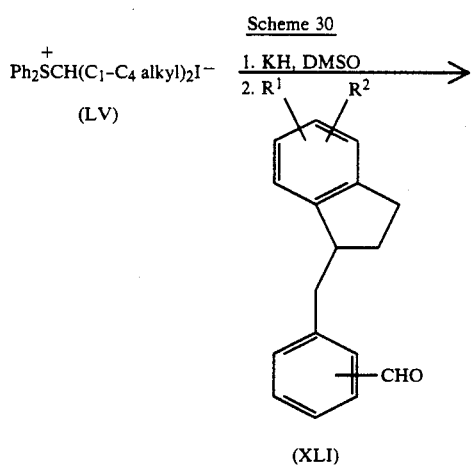

(XLI)

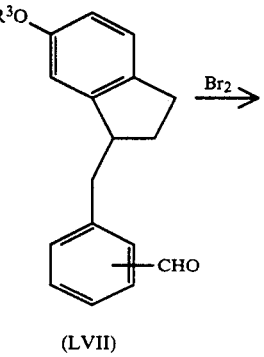

(LVI)

$R^6$ is $C_1$-$C_4$ alkyl

The compounds of formula (I), in which $R^1$ is 6—$OR^3$, $R^2$ is 5—$CO_2H$, and X is of formula (II), wherein one $R^4$ is hydrogen and the other $R^4$ is $C_1$-$C_4$ alkyl or hydrogen, may be prepared from compounds of formula (LVII). Thus, treatment of (LVII) with bromine, in a manner described in House, "Modern Synthetic Reactions," pp.428-30, W. A. Benjamin, Inc., Menlo Park, Calif., 1972, could provide compounds of formula (LVIII). Treatment of (LVIII) with (LIII), analogous to Scheme 29, could provide compounds of formula (LIX). Treatment of (LIX) with n-butyllithium followed by addition of carbon dioxide, in a manner similar to that described by Gilman, Willis, and Swislowsky, *J. Am. Chem. Soc.*, 61, 1371 (1939), could provide compounds of formula (LX). This is shown in Scheme 31.

Scheme 31

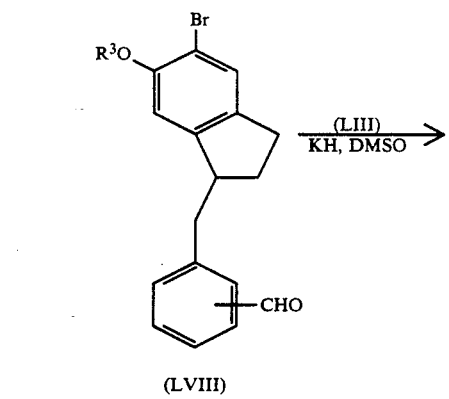

(LVII)

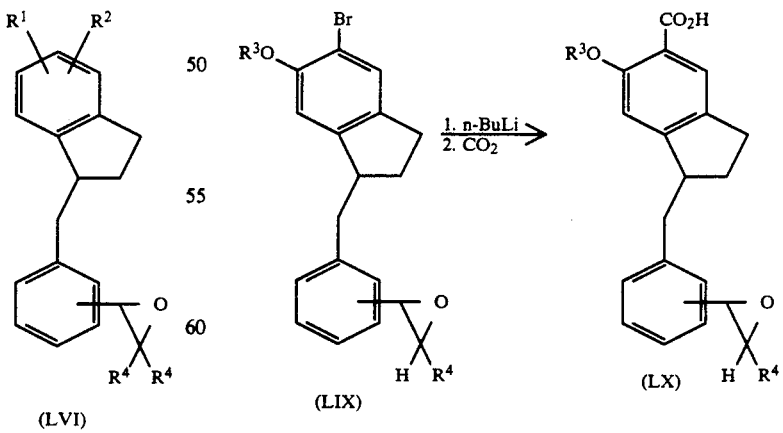

(LVIII)

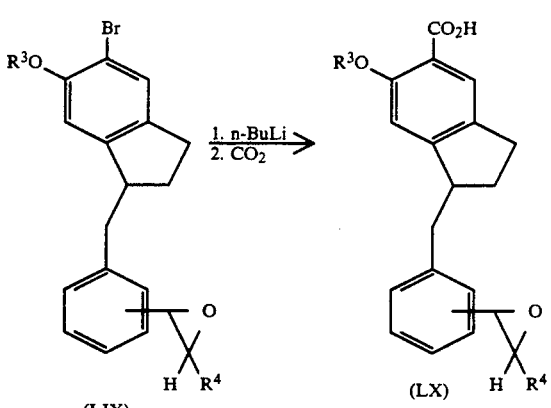

(LIX)            (LX)

The compounds of formula (I), in which $R^4$ is 6—$OR^3$, $R^2$ is 5—$CO_2H$, and X is of formula (II), wherein $R^4$ is $C^1$-$C^4$ alkyl, could be prepared from compounds of formula (LVIII). Thus, treatment of (LVIII) with (LV), in a manner analogous to that in Scheme 30, could provide compounds of the Formula (LXI). Treatment of (LXI) with n-butyllithium followed by carbon dioxide, in a manner analogous to that in Scheme 31, could provide compounds of formula (LXII). This is shown in Scheme 32.

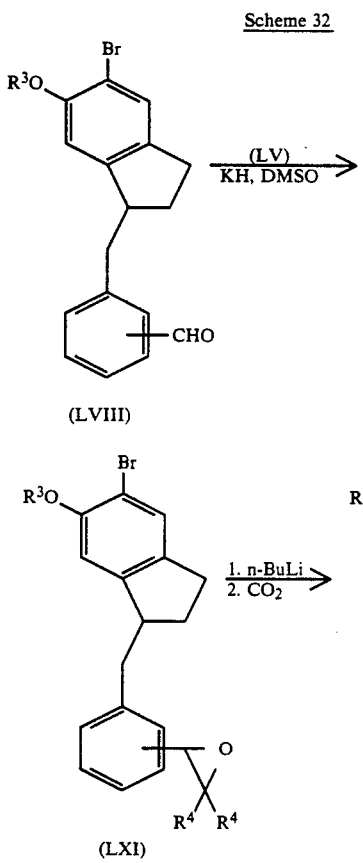

The compounds of formula (I), in which $R^1$ is 6—$OR^3$, $R^2$ is 5—$CO_2R^3$, and X is of formula (II), could be prepared from compounds of the Formula (LXII). Thus, treatment of (LXII) with a $C_1$-$C_4$ diazoalkane, in a manner analogous to that in Scheme 2, could provide compounds of formula (LXIII). This is shown in Scheme 33.

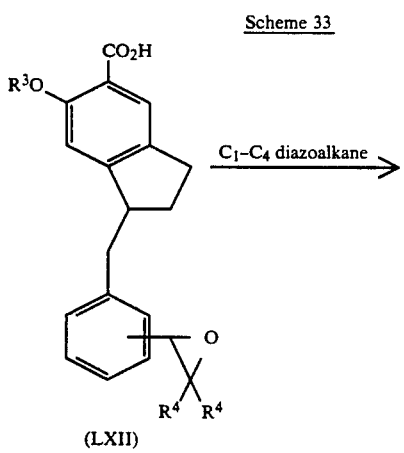

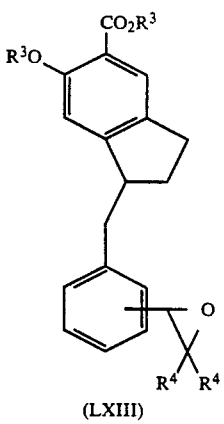

The compounds of formula (I), in which X is $CF_2CHO$, could be prepared from compounds of formula (LXIV). Thus, treatment of (LXIV) with thionyl chloride, in a manner similar to that described in March, "Advanced Organic Chemistry Reactions, Mechanisms, and Structure, " pp. 346-7, McGraw-Hill, Inc., New York, 1968, could lead to formation of compounds of formula (LXV). Treatment of (LXV) with sodium cyanide, in a manner similar to that described by Koenig and Weber, *Tetrahedron Lett.*, 2275 (1974), could provide compounds of formula (LXVI). Treatment of (LXVI) with sulfuric acid followed by methanol, in a manner similar to that described by Photis, *Tetrahedron Lett.*, 3539 (1980), could provide compounds of formula (LXVIII). Conversion of (LXVII) to (LXVIII) could take place upon treatment of (LXVII) with diethylaminosulfur trifluoride, in a manner similar to that described by Middleton, *J. Org. Chem.*, 40 574 (1975). Reduction of (LXVIII) could be effected by treatment with diisobutylaluminum hydride, in a manner similar to that described in Fieser and Fieser, "Reagents for Organic Synthesis, " Vol. 1, pp. 260-2, John Wiley and Sons, Inc., New York, 1967, to provide compounds of formula (LXIX). This is shown in Scheme 34.

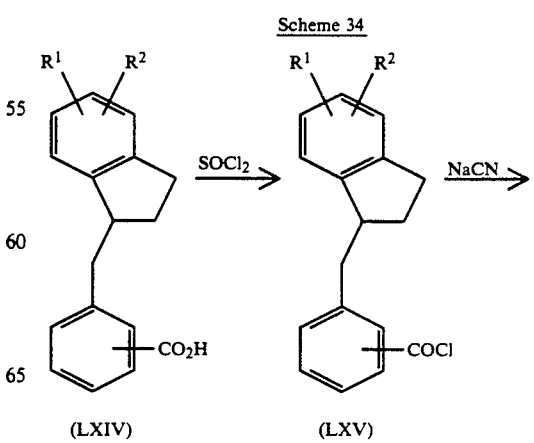

-continued
Scheme 34

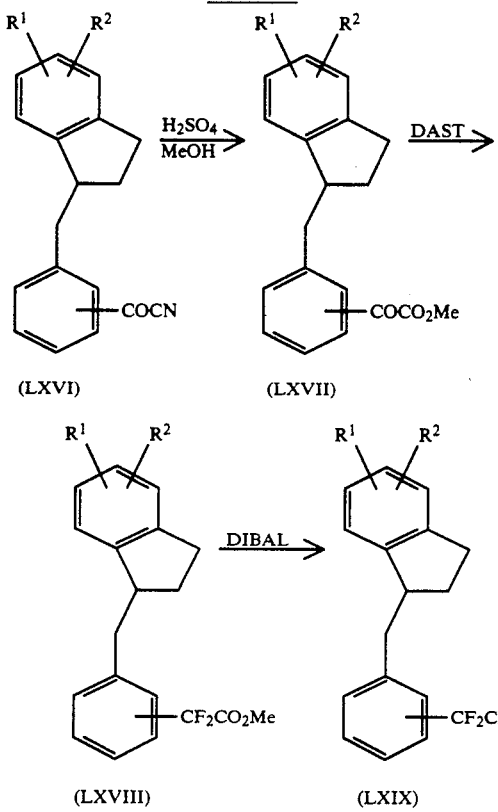

The compounds (I), in which X is CF2CH2OH, could be prepared from compounds of formula (LXIX). Thus, treatment of (LXIX) with sodium borohydride, in a manner analogous to the conversion of (XLII) to (XLIII) in Scheme 23, could provide compounds of the Formula (LXX). This is shown in Scheme 35.

Scheme 35

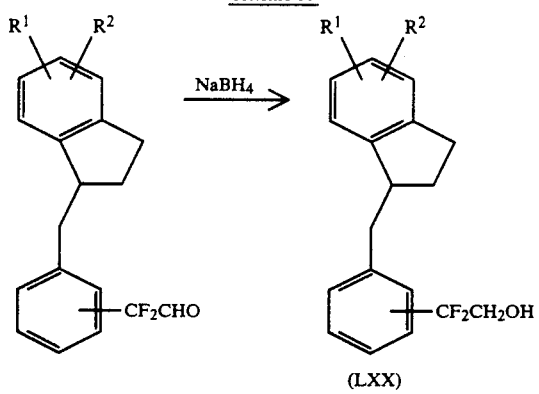

The compounds of formula (I), in which $R^1$ is 6—$OR^3$, $R^2$ is 5—CO2H and X is CH2CHO, could be prepared from compounds of formula (LXXI). Thus, treatment of (LXXI) with methanol and dry hydrochloric acid, in a manner similar to that described in Greene, "Protective Groups in Organic Synthesis," p.117, Wiley-Interscience, Inc., New York, 1981, could provide compounds of the Formula (LXXII). Treatment of (LXXII) with bromine could provide compounds of formula (LXXIII). Treatment of (LXXIII) with n-butyllithium followed by carbon dioxide, in a manner similar to that described in Scheme 31, could lead to compounds of formula (LXXIV) after treatment with dilute sulfuric acid. This is shown in Scheme 36.

Scheme 36

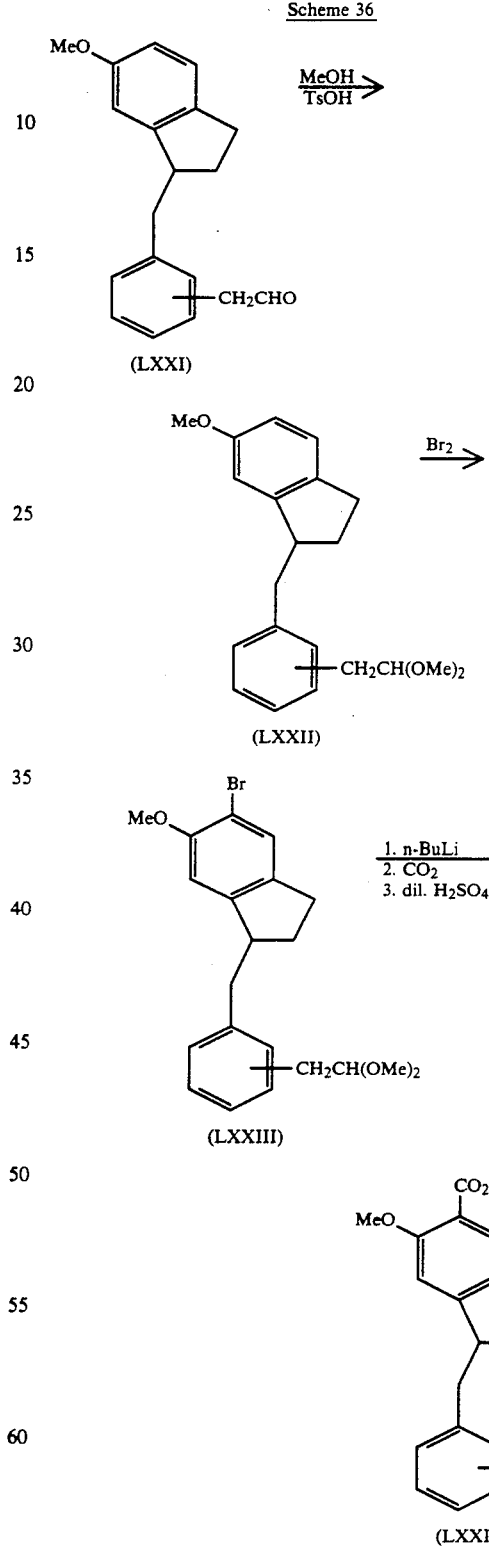

The Compounds of formula (I), in which $R^1$ is 6—$OR^3$, $R^2$ is 5—$CO_2R^3$ and X is CH2CHO, could be prepared from compounds of formula (LXXIV). Thus, treatment of (LXXIV) with a base, for example potassium carbonate, in the presence of a C1–C4 alkyl iodide, could provide compounds of formula (LXXV). The method is analogous to that for the conversion of (XIV) to (XV) in Scheme 7, and is shown in Scheme 37.

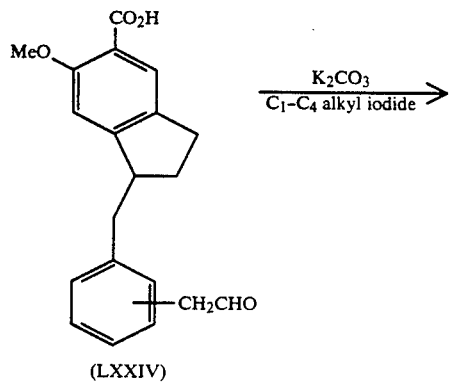

Scheme 37

(LXXIV)

(LXXIV)

The compounds of formula (I), in which neither $R^1$ nor $R^2$ is $CO_2R^4$ and X is $B(OH)_2$, could be prepared from compounds of formula (LXXVI). Thus, treatment of (LXXVI) with nitrous acid followed by copper (I) bromide, in a manner similar to that described in March, "Advanced Organic Chemistry: Reactions, Mechanisms, and Structure," p. 554, McGraw-Hill, Inc. New York, 1968, would lead to formation of compounds of formula (LXXVII). Treatment of (LXXVII) with magnesium followed by n-butylborate and then dilute hydrochloric acid, similar to that described by Bean and Johnson, *J. Am. Chem., Soc.*, 54 4415 (1932), is expected to lead to formation of compounds of the formula (LXXVIII). This is shown in Scheme 38.

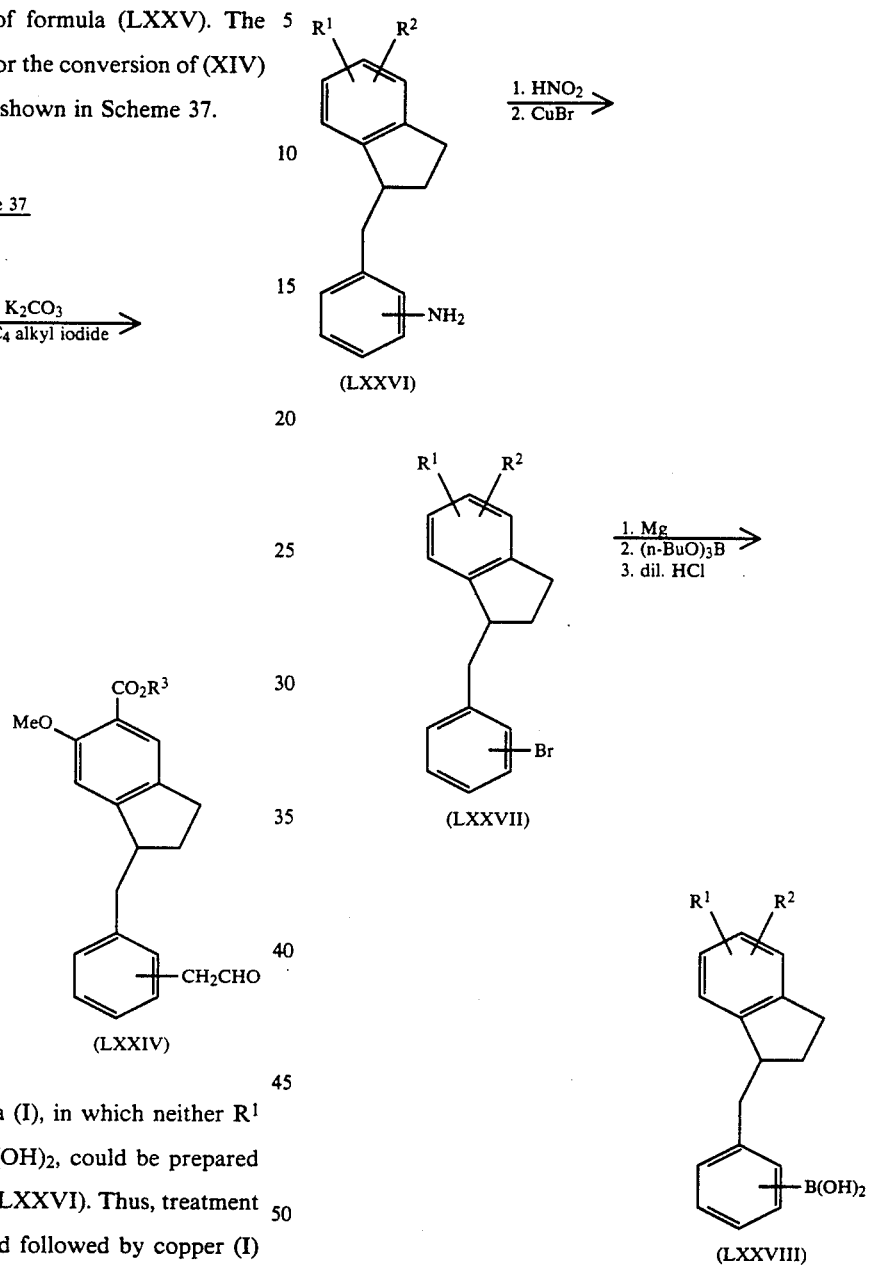

Neither $R^1$ nor $R^2$ is $CO_2R^4$

The compounds of formula (I), in which neither $R^1$ nor $R^2$ is $CO_2R^4$ and X is of formula (IIA), could be prepared from compounds of formula (LXXIX). Thus, treatment of (LXXIX) with sodium azide followed by acidification with dilute hydrochloric acid, similar to that reviewed by Kadaba, *Synthesis*, 71 (1973), would lead to formation of compounds of formula (LXXX). This is shown in Scheme 39.

Scheme 39

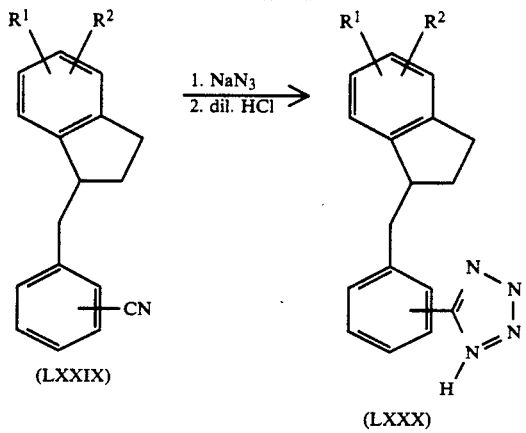

Neither $R^1$ nor $R^2$ is $CO_2R^4$

EXAMPLES

Reactions requiring anhydrous conditions are performed in flame-dried glassware and dry solvent was distilled prior to use following standard laboratory practices known to those skilled in the art of organic synthesis. Standard analytical equipment was used for sample purification and analyses.

EXAMPLE 1

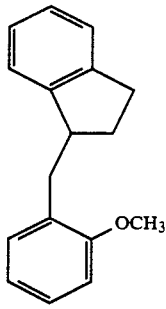

2-(2',3'-Dihydroinden-1'-ylmethyl)-anisole

A mixture of 11.6 g (100 mmol) of indene and 75 mL dry tetrahydrofuran was stirred at −78° C. under nitrogen. To this solution was added dropwise 62.5 mL (100 mmol) of 1.6 M n-butyllithium in hexane. After stirring the mixture for 30 mins, a solution of 22.1 g (110 mmol) of 2-methoxybenzyl bromide in 100 mL dry tetrahydrofuran was added dropwise. The mixture was stirred for an additional 3 hrs before warming to room temperature and quenching with water. The aqueous mixture was extracted with 3×100 mL ethyl acetate. The organic layers were combined, dried over anhydrous magnesium sulfate, filtered, and the solvent was removed. The residue was hydrogenated over 500 mg of 10% palladium-on-carbon in absolute ethanol at 50 psi for 2 hrs. The mixture was filtered and the solvent was removed. The residue was purified by chromatography on silica gel using hexanes. The solid obtained was 13.0 g (54.6 mmol, 55%) of 2-(2',3'-dihydroinden-1'-ylmethyl)-anisole, mp=49°-51° C. NMR(CDCl₃): ∂1.7–3.55(m, 7 H), 3.8(s, 3 H), 6.85–7.25(m, 8 H). IR(Nujol): 2926 cm⁻¹. High resolution mass spectrum: calculated: 238.1358; measured: 238.1358.

EXAMPLE 2

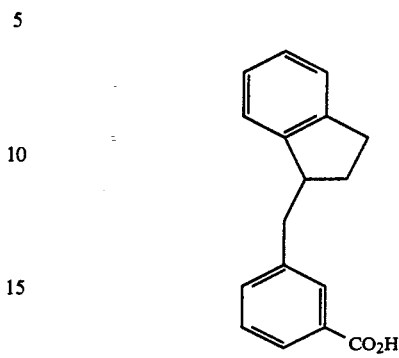

3-(2',3'-Dihydroinden-1'-ylmethyl)-benzoic acid

Step A: Preparation of Z-3-(2',3'-dihydro-1H-inden-1'-ylmethyl)-benzonitrile and E-3-(2',3'-dihydro-1H-inden-1'-ylmethyl)-benzonitrile A mixture of 9.5 q (83 mmol) of potassium hydride (35% oil dispersion) and 200 mL of dry tetrahydrofuran was stirred at room temperature under nitrogen. To this was added 38 g (83 mmol) of 3-cyanobenzyltriphenylphosphonium bromide, portionwise, over 5 mins. The mixture was allowed to stir for 30 mins when a solution of 10.96 g (83 mmol) of 1-indanone in 20 mL dry tetrahydrofuran was added dropwise at room temperature. The mixture was then set at reflux overnight. The reaction mixture was allowed to cool to room temperature and 5 mL of methanol was added dropwise. The mixture was poured into 200 mL of water and extracted with 3×100 mL of ethyl acetate. The organic layers were combined, dried over anhydrous magnesium sulfate, filtered, and the solvent was evaporated. The residue was purified by column chromatography on silica gel using 19:1 hexanes/ethyl acetate. The product obtained was 2.0 g (8.6 mmol, 10%) of Z-3-(2',3'-dihydro-1H-inden-1'-ylmethyl)-benzonitrile as an oil. NMR(CDCl₃): ∂2.4(s, 4 H), 6.5–7.7(m, 9 H). IR(Nujol): 2228 cm⁻¹. High resolution mass spectrum: calculated: 231.1048; measured: 231.1046. A more polar fraction was also obtained, consisting of 6.4 g (27.5 mmol, 32%) of E-3-(2',3'-dihydro-1H-inden-1'-ylmethyl)-benzonitrile as a solid, mp=87°-88° C. NMR(CDCl₃): ∂3.1 (s, 4 H), 6.9 (s, 1 H), 7.2–7.8 (m, 8 H). IR(Nujol): 2227 cm⁻¹. High resolution mass spectrum: calculated: 231.1048; measured: 231.1046.

Step B: Preparation of E-3-(2',3'-dihydro-1H-inden-1'-ylmethyl)-benzoic acid

A mixture of 2.0 g (8.6 mmol) of E-3-(2',3'-dihydro-1H-inden-1'-ylmethyl)-benzonitrile, 5 mL ethanol, and 10 mL of 50% sodium hydroxide was stirred at reflux under nitrogen for one hour. The mixture was allowed to cool to room temperature and was acidified to pH 1 with 5 N hydrochloric acid. The solid precipitated was filtered and dried to provide 2.0 g (8.0 mmol, 93%) of E-3-(2',3'-dihydro-1H-inden-1'-ylmethyl)-benzoic acid, mp=185°-187° C. NMR(CDCl₃): ∂3.1(s, 4 H), 7.0(s, 1 H), 7.2–8.0(m, 8 H), 8.25(s, 1 H). IR(Nujol): 3340, 1695 cm⁻¹. High resolution mass spectrum: calculated: 250.0993; measured: 250.0998.

Step C: Preparation of
3-(2',3'-dihydroinden-1'-ylmethyl)-benzoic acid

A mixture of 1.3 g (5.2 mmol) E-3-(2',3'-dihydro-1H-inden-1'-ylmethyl)-benzoic acid, 50 mL absolute ethanol, and 150 mg of 10% palladium-on-carbon was hydrogenated at 50 psi for 1.5 hrs at room temperature. The mixture was filtered and washed with absolute ethanol. The solvent was evaporated from the filtrate to provide 1.1 g (4.4 mmol, 85%) of 3-(2',3'-dihydroinden-1'-ylmethyl) benzoic acid, mp=133°-134° C. NMR(CDCl$_3$): d1.65-3.55(m, H), 7.05-7.5(m, 7 H), 8.0(m, 2 H). IR(Nujol): 1688 cm$^{-1}$. High resolution mass spectrum: calculated: 252.1150; measured: 252.1151.

EXAMPLE 3

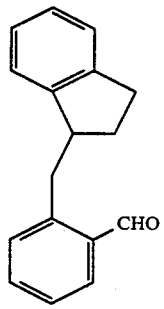

2-(2',3'-Dihydroinden-1'-ylmethyl)-benzaldehyde

This compound was prepared analogous to Example 4 from 2-(2',3'-dihydroinden-1'-ylmethyl)-benzonitrile. The product obtained was 1.7 g (7.2 mmol, 55%) of 2-(2',3'-dihydroinden-1'-ylmethyl)-benzaldehyde as an oil. NMR(CDCl$_3$): ∂1.5-3.7(m, 7 H), 6.8-8.9(m, 8 H), 10.3(s, 1 H). IR(Neat): 1697 cm$^{-1}$. Mass spectrum(EI): M/z=236.

EXAMPLE 4

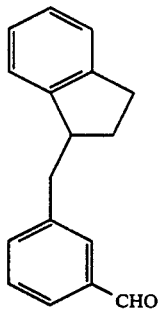

3-(2',3'-Dihydroinden-1'-ylmethyl)-benzaldehyde

To a mixture of 80 g (346 mmol) of 3-(2',3'-dihydroinden-1'-ylmethyl)-benzonitrile and 500 mL toluene stirred at −78° C. under nitrogen, was added dropwise a solution of 346 mL (519 mmol) of 1.5 M diisobutylaluminum hydride in toluene. The mixture was stirred at −78° C. for 2 hrs. The mixture was allowed to warm to room temperature and 200 mL of 1 N acetic acid was added dropwise. The mixture was extracted with 3×200 mL ethyl acetate, and the organic layers were combined and washed with brine. The organic mixture was dried over anhydrous magnesium sulfate, filtered, and the solvent was removed to provide 28.6 g (121 mmol, 35%) of 3-(2',3'-dihydroinden-1'-ylmethyl)-benzaldehyde as an oil. NMR(CDCl$_3$): ∂1.7-3.6(m, 7 H), 7.05-7.8(m, 8 H), 10.0(s, 1 H). IR(Neat): 1702 cm$^{-1}$. High resolution mass spectrum: calculated: 236.1201; measured: 236.1221.

EXAMPLE 5

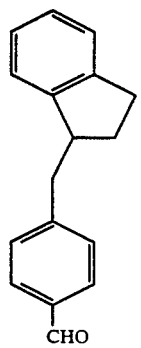

4-(2',3'-Dihydroinden-1'-ylmethyl)-benzaldehyde

This compound was prepared analogous to Example 4 from 4-(2',3'-dihydroinden-1'-ylmethyl)-benzonitrile. The product obtained was 2.6 g (11 mmol, 85%) of 4-(2',3'-dihydroinden-1'-ylmethyl)-benzaldehyde, mp=61°-63° C. NMR(CDCl$_3$): ∂1.7-3.55(m, 7 H), 7.05-7.8(m, 8 H), 10.0(s, 1 H). IR(KBr): 1694 cm$^{-1}$. High resolution mass spectrum: calculated: 236.1201; measured: 236.1199.

EXAMPLE 6

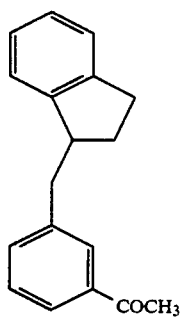

3-(2',3'-Dihydroinden-1'-ylmethyl)-acetophenone Step A: Preparation of
E-3-(2',3'-dihydro-1H-inden-1'-ylmethyl)-acetophenone To a mixture of 4.85 g (21 mmol) of E-3-(2',3'-dihydro-1H-inden-1'-ylmethyl)-benzonitrile and 25 mL dry tetrahydrofuran stirred at room temperature under nitrogen, was added dropwise a mixture of 14 mL (42 mmol) of 3.0 M methylmagnesium chloride in tetrahydrofuran. The mixture was stirred for 1 hr at room temperature followed by reflux overnight. The reaction mixture was allowed to cool to room temperature and was quenched by pouring carefully into 100 mL of 1 N hydrochloric acid. The mixture was extracted with 3×100 mL ethyl acetate followed by 1×100 mL methylene chloride. The organic layers were combined, dried over anhydrous magnesium sulfate, filtered, and the solvent was evaporated. The residue was purified by column chromatography on silica gel using 19:1 hexanes/ethyl acetate to provide 1.07 g (4.3 mmol, 20%) of E-3-(2',3'-dihydro-1H-inden-1'-ylmethyl)-acetophenone as a solid, mp=71°-73° C. NMR(CDCl₃): ∂2.65(s, 3 H), 3.15(s, 4 H), 7.0-8.1(m, 8 H). IR(Nujol): 1680 cm⁻¹. High resolution mass spectrum: calculated: 248.1201; measured: 248.1206.

Step B: Preparation of 3-(2',3'-dihydroinden-1'-ylmethyl)-acetophenone

A mixture of 900 mg (3.6 mmol) of E-3-(2',3'-dihydro-1H-inden-1'-ylmethyl)-acetophenone, 100 mg of 10% palladium-on-carbon, and 100 mL of absolute ethanol was hydrogenated at 50 psi for 1 hr. The mixture was filtered, washed with absolute ethanol, and the solvent was evaporated from the filtrate. The residue was purified by column chromatography on silica gel using 9:1 hexanes/ethyl acetate to provide 700 mg (2.8 mmol, 78%) of 3-(2',3'-dihydroinden-1'-ylmethyl-)acetophenone as an oil. NMR(CDCl₃): ∂1.8(m, 1 H), 2.2(m, 1 H), 2.6(s, 3 H), 2.8(m, 3H), 3.2(m, 1H), 3.5(m, 1 H), 7.05-7.85(m, 8 H). IR(Neat): 1683 cm⁻¹. High resolution mass spectrum: calculated: 250.1357; measured: 250.1360.

EXAMPLE 7

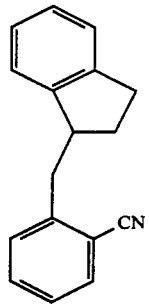

2-(2',3'-Dihydroinden-1'-ylmethyl)-benzonitrile

This compound was prepared analogous to Example 8 from indene and 2-(bromomethyl)-benzonitrile. The product obtained was 11.6 g (49.8 mmol, 40%) of 2-(2',3'-dihydroinden-1'-ylmethyl)-benzonitrile, mp=55°-57° C. NMR(CDl₃): ∂1.75-3.6(m, 7 H), 7.1-7.7(m, 8 H). IR(Neat) 2223 cm⁻¹. High resolution mass spectrum: calculated: 233.1204; measured: 233.1213.

EXAMPLE 8

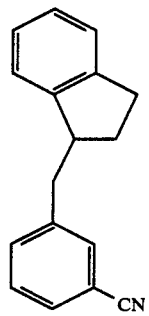

3-(2',3'-Dihydroinden-1'-ylmethyl)-benzonitrile

A mixture of 73.52 g (634 mmol) of indene and 200 mL dry tetrahydrofuran was stirred at −78° C. under nitrogen. A solution of 390 mL (634 mmol) of 1.6 M n-butyllithium in hexane was added dropwise and the mixture was stirred for 30 mins. A solution of 125 g (634 mmol) of 3-(bromomethyl)-benzonitrile in 100 mL dry tetrahydrofuran was added dropwise, and the mixture was stirred for 3 hrs at −78° C. After the addition of 20 mL of water in a dropwise manner, the mixture was allowed to warm to room temperature and added to 300 mL of water. The mixture was extracted with 3×200 mL of ethyl acetate. The organic layers were combined, washed with brine, and dried over anhydrous magnesium sulfate. The mixture was filtered and solvent was removed. The residue was dissolved in 500 mL absolute ethanol and 15 g of 10% palladium-on-carbon was added. The mixture was hydrogenated at 50 psi for 2 hrs, filtered, and the solvent was removed. The residue was purified by column chromatography using 9:1 hexanes/ethyl acetate to provide 80 g (346 mmol, 55%) of 3-(2',3'-dihydroinden-1'-ylmethyl)-benzonitrile, mp=71°-72° C. NMR(CDCl₃): ∂1.65-3.5(m, 7 H), 7.0-7.6(m, 8 H). IR(Nujol): 2225 cm⁻¹. High resolution mass spectrum: calculated: 233.1204; measured: 233.1216.

EXAMPLE 9

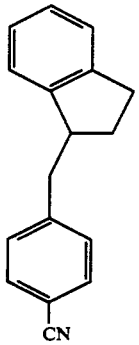

4-(2',3'-Dihydroinden-1'-ylmethyl)-benzonitrile

This compound was prepared analogous to Example 8 from indene and 4-(bromomethyl)-benzonitrile. The product obtained was 83.5 g (358 mmol, 56%) of 4-(2',3'-dihydroinden-1'-ylmethyl)-benzonitrile, mp=108°-109° C. NMR(CDCl₃): ∂1.65-3.55(m, 7 H), 7.0–7.6(m, 8 H). IR(Nujol): 2224 cm−1. High resolution mass spectrum: calculated: 233.1204; measured: 233.1211.

EXAMPLE 10

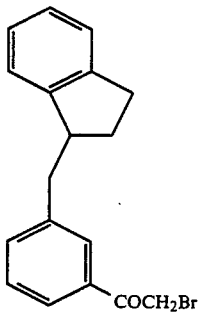

3-(2',3'-Dihydroinden-1'-ylmethyl)-alpha-bromoacetophenone

To a mixture of 4.5 g (18 mmol) of 3-(2',3'-dihydroinden-1'-ylmethyl)-acetophenone and 30 mL of glacial acetic acid stirred at room temperature under nitrogen, was added dropwise 2.88 g (18 mmol) of bromine. After stirring for an additional 30 mins., the mixture was poured into water and extracted with 3×100 mL ethyl acetate. The organic layers were combined, dried over anhydrous magnesium sulfate, and filtered. The solvent was removed. The residue was purified by column chromatography on silica gel using 18:1:1 hexanes/ethyl acetate/methylene chloride to provide 2.5 g (7.5 mmol, 42%) of 3-(2',3'-dihydroinden-1'-ylmethyl)-alpha-bromoacetophenone as an oil. NMR(CDCl3): ∂1.8(m, 1 H), 2.15(m, 1 H), 2.8(m, 3 H), 3.2(m, 1 H), 3.5(m, 1 H), 4.45(s, 2 H), 7.1–7.9(m, 8 H). IR(Neat): 1699 cm−1. High resolution mass spectrum: calculated: 250.1357; measured: 250.1360.

EXAMPLE 11

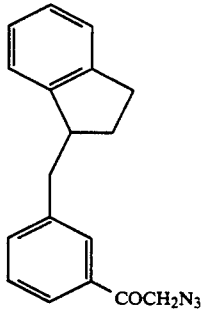

3-(2',3'-Dihydroinden-1'-ylmethyl)-alpha-azidoacetophenone

A mixture of 204 mg (3.1 mmol) of sodium azide, 2 mL water and 1 mL methanol was stirred under nitrogen at room temperature. A mixture of 1.0 g (3.0 mmol) of 3-(2',3'-dihydroinden-1'-ylmethyl)-alpha-bromoacetophenone in 1 mL of methanol was added and the mixture was heated on a steam bath for 24 hrs. The mixture was allowed to cool to room temperature and poured into water. The mixture was extracted with 3×100 mL of ether. The organic layers were combined, washed with water, brine, dried over anhydrous magnesium sulfate, and filtered. The solvent was removed in vacuo. The residue was purified by column chromatography on silica gel using 19:1 hexanes/ethyl acetate to provide 330 mg (1.1 mmol, 36%) of 3-(2',3'-dihydroinden-1'-ylmethyl)-alpha-azidoacetophenone as an oil. NMR(CDCl3): ∂1.75(m, 1 H), 2.1(m, 1 H), 2.75(m, 3 H), 3.15(m, 1 H), 3.45(m, 1 H), 4.5(s, 2 H), 7.0–7.75(m, 8H). IR(Neat): 2106, 1697 cm−1. High resolution mass spectrum: calculated: 291.1371; measured: 291.1372.

EXAMPLE 12

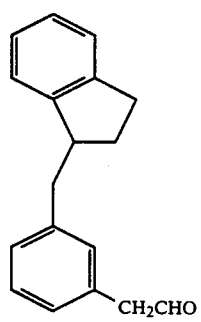

3-(2',3'-Dihydroinden-1'-ylmethyl)-phenylacetaldehyde

To a mixture of 2.3 g (20 mmol) of potassium hydride (35% oil dispersion) and 100 mL dry tetrahydrofuran stirred at room temperature under nitrogen was added, portionwise over 5 mins, 6.84 g (20 mmol) of (methoxymethyl)triphenylphosphonium chloride. After stirring the mixture for 30 mins., a solution of 2.36 g (10 mmol) of 3-(2',3'-dihydroinden-1'-ylmethyl)benzaldehyde in 10 mL dry tetrahydrofuran was added dropwise. The mixture was stirred at reflux for 72 hrs., after which time it was allowed to cool to room temperature and quenched with 10 mL methanol. The mixture was poured into water and extracted with 3×100 mL ethyl acetate. The organic layers were combined, dried over anhydrous magnesium sulfate, and filtered. The solvent was removed in vacuo. The residue was purified by column chromatography on silica gel using 9:1 hexanes/ethyl acetate. The resulting oil was treated with a mixture of 50 mL tetrahydrofuran and 50 mL of 1 M hydrochloric acid. The mixture was heated at reflux for 1 hr under nitrogen. The reaction mixture was allowed to cool to room temperature and was extracted with 3×50 mL ethyl acetate. The organic layers were combined, dried over anhydrous magnesium sulfate, and filtered. The solvent was removed in vacuo. The residue was purified by column chromatography on silica gel using 14:1 hexanes/ethyl acetate. The product obtained was 560 mg (2.24 mmol, 22%) of 3-(2',3'-dihydroinden-1'-ylmethyl)phenylacetaldehyde as an oil. NMR(CDCl3): ∂1.7–3.55(m, 7 H), 3.65(d, 2 H), 7.0–7.35(m, 8 H), 9.7(t, 1 H). IR(Neat): 1724 cm−1. High resolution mass spectrum: calculated: 250.1358; measured: 250.1387.

EXAMPLE 13

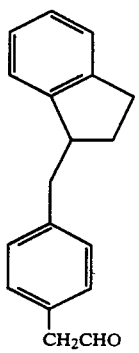

4-(2′,3′-dihydroinden-1′-ylmethyl1)-phenylacetaldehyde

This compound was prepared analogous to Example 11 from 4-(2′,3′-dihydroinden-1′-ylmethyl)-benzaldehyde. The product obtained was 190 mg (0.76 mmol, 25%) of 4-(2′,3′-dihydroinden-1′-ylmethyl)-phenylacetaldehyde as an oil. NMR(CDCl$_3$): ∂1.7–3.5(m, 7 H), 3.7(d, 2H), 7.05–7.25(m, 8 H), 9.75(m, 1 H). IR(Neat): 1724 cm$^{-1}$. High resolution mass spectrum: calculated: 250.1358; measured: 250.1365.

EXAMPLE 14

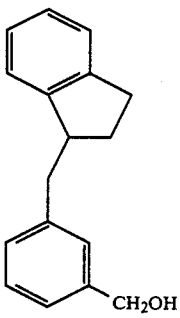

3-(2′,3′-dihydroinden-1′-ylmethyl)-benzyl alcohol

A mixture of 800 mg (21.15 mmol) of lithium aluminum hydride and 25 mL dry tetrahydrofuran was stirred at room temperature under nitrogen. A solution of 1.0 g (4.23 mmol) of 3-(2′,3′-dihydroinden-1′-ylmethyl)-benzaldehyde in 1 mL dry tetrahydrofuran was added dropwise. The mixture was stirred at reflux overnight and was then allowed to cool to room temperature. The mixture was carefully quenched by the sequential, dropwise addition of 0.8 mL water, 0.8 mL of 15% sodium hydroxide, and 2.4 mL water. Anhydrous magnesium sulfate was added and the mixture was filtered and the solvent removed in vacuo. The resulting solid was triturated under hexanes to provide 800 mg (3.36 mmol, 79%) of 3-(2′,3′-dihydroinden-1′-ylmethyl)-benzyl alcohol, mp=68°–70° C. NMR(CDCl$_3$): ∂1.5–3.5(m, 8 H), 4.7(d, 2 H), 7.1–7.3(m, 8 H). IR(Nujol): 3239 cm$^{-1}$. Mass spectrum(EI): M/z=238.

EXAMPLE 15 3-(2′,3′-dihydroinden-1′-ylmethyl)-benzylamine

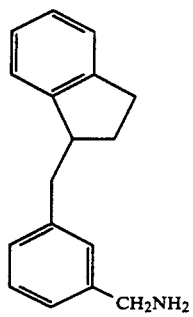

To a mixture of 380 mg (10 mmol) of lithium aluminum hydride and 15 mL dry tetrahydrofuran stirred at room temperature under nitrogen was added 2.38 g (10 mmol) of 3-(2′,3′-dihydroinden-1′-ylmethyl)-benzonitrile. The mixture was stirred at reflux overnight. The reaction mixture was allowed to cool to room temperature and carefully quenched by the dropwise addition of water. The mixture was then added to water and was extracted with 3×100 mL ethyl acetate. The organic layers were combined, dried over anhydrous magnesium sulfate, and filtered. The solvent was removed in vacuo. The residue was purified by column chromatography on silica gel using 4:1 methanol/ethyl acetate. The product obtained was 1.28 g (5.4 mmol, 54%) of 3-(2′,3′-dihydroinden-1′-ylmethyl)-benzylamine as an oil. NMR(CDCl$_3$): ∂1.7–3.5(m, 9 H), 3.85(s, 2 H), 7.1–7.3(m, 8 H). Ir(neat): 3377, 3289 cm$^{-1}$. High resolution mass spectrum: calculated: 237.1518; measured: 237.1518.

EXAMPLE 16

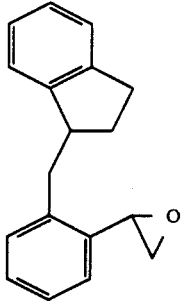

Diastereomeric mixture of 2-(2′,3′-dihydroinden-1′-ylmethyl)-oxiranylbenzenes

This mixture of compounds was prepared analogous to Example 17 (see below) from 2-(2′,3′-dihydroinden-1′-ylmethyl)-benzaldehyde. The product obtained was 330 mg (1.3 mmol, 17%) of a diastereomeric mixture of 2-(2′,3′-dihydroinden-1′-ylmethyl)-oxiranylbenzenes as an oil. NMR(CDCl$_3$): ∂1.7–3.5(m, 9 H), 3.9(m, 1 H), 6.9–7.3(m, 8 H). IR(Neat): 2935 cm$^{-1}$. High resolution mass spectrum: calculated: 250.1358; measured: 250.1360.

EXAMPLE 17

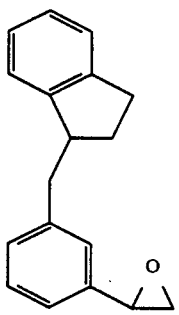

Diastereomeric mixture of
3-(2',3'-dihydroinden-1'-ylmethyl)-oxiranylbenzenes

To a mixture of 910 mg (8.0 mmol) of potassium hydride (35% oil dispersion) and 5 mL dry tetrahydrofuran stirred at room temperature under nitrogen was added dropwise 10 mL dry dimethylsulfoxide. After stirring for 5 mins., the mixture was cooled to −10°-0° C. A mixture of 1.63 g (8.0 mmol) of trimethylsulfonium iodide in 3 mL dry dimethylsulfoxide was added dropwise and the mixture was stirred for 5 mins. A solution of 1.60 g (6.7 mmol) of 3-(2',3'-dihydroinden-1'-ylmethyl)-benzaldehyde in 3 mL dry tetrahydrofuran was added, and the mixture was stirred at 0° C. for 30 mins and then at room temperature for 1 hr. Methanol (5 mL) was added dropwise and the mixture was poured into 50 mL water and extracted with 7×50 mL diethyl ether. The organic layers were combined, dried over anhydrous magnesium sulfate, and filtered. The solvent was removed in vacuo. The residue was purified by column chromatography on silica gel using 9:1 hexanes/ethyl acetate to provide 780 mg (3.12 mmol, 47%) of a diastereomeric mixture of 3-(2',3'-dihydroinden-1'-ylmethyl)-oxiranylbenzenes as an oil. NMR(CDCl$_3$): ∂1.7(m, 1 H), 2.05(m, 1 H), 2.55-3.15(m, 6 H), 3.4(m, 1 H), 3.8(bm, 1 H), 6.95-7.25(m, 8 H). IR(Neat): 2934 cm$^{-1}$. High resolution mass spectrum: calculated: 250.1358; measured: 250.1365.

EXAMPLE 18

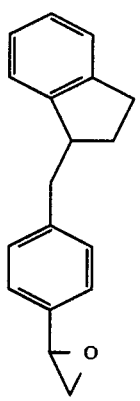

Diastereomeric mixture of
4-(2',3'-dihydroinden-1'-ylmethyl)-oxiranylbenzenes

This mixture of compounds was prepared analogous to Example 17 from 4-(2',3'-dihydroinden-1'-ylmethyl)-benzaldehyde. The product obtained was 920 mg (3.7 mmol, 49%) of a diastereomeric mixture of 4-(2',3'-dihydroinden-1'-ylmethyl)-oxiranylbenzenes as an oil. NMR(CDCl$_3$): ∂1.7-3.85(m, 10 H), 7.05-7.25(m, 8 H). IR(Neat): 2920 cm$^{-1}$. High resolution mass spectrum: calculated: 250.1358; measured: 250.1360.

EXAMPLE 19

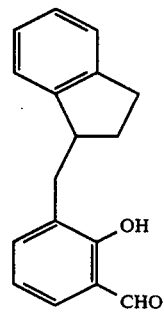

3-(2',3'-dihydroinden-1'-ylmethyl)-2-hydroxybenzaldehyde

To a mixture of 1.54 g (6.9 mmol) of 2-(2',3'-dihydroinden-1'-ylmethyl)-phenol and 3 mL of 95% ethanol stirred at room temperature under nitrogen was added, rapidly, a solution of 2.0 g (50 mmol) of sodium hydroxide in 4.5 mL water. The mixture was heated at 70°-80° C. and 1.31 g (11 mmol) of chloroform was added dropwise, maintaining the temperature between 70°-80° C. The mixture was stirred at this temperature for 1 hr after complete addition. The solvent was removed and 1.75 mL concentrated hydrochloric acid was carefully added. Water was added and the mixture was extracted with 3×100 mL ethyl acetate. The organic layers were combined, dried over anhydrous magnesium sulfate, and filtered. The solvent was removed in vacuo. The residue was purified by chromatography on silica gel using 9:1 hexanes/ethyl acetate. The product obtained was 400 mg (1.58 mmol, 23%) of 3-(2',3'-dihydroinden-1'-ylmethyl)-2-hydroxybenzaldehyde as an oil. NMR(CDCl$_3$): ∂1.6-3.6(m, 7 H), 6.8-7.4(m, 7 H), 9.85(s, 1 H), 11.25(s, 1 H). IR(Neat): 1652 cm$^{-1}$. High resolution mass spectrum: calculated: 252.1150; measured: 252.1151.

Table I contains additional preferred embodiments of this invention. However, these embodiments are not exemplified herein.

TABLE I

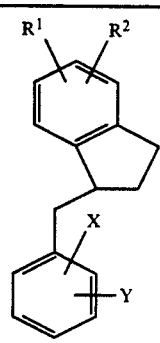

| Ex | R$^1$ | R$^2$ | X | Y |
|---|---|---|---|---|
| 20 | H | H | 3-COCH$_3$ | H |

TABLE I-continued

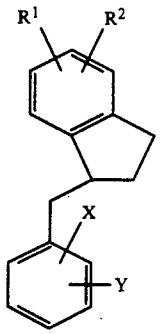

| Ex | R¹ | R² | X | Y |
|---|---|---|---|---|
| 21 | H | H | 4-COCH₃ | H |
| 22 | H | H | 2-CO(CH₂)₃CH₃ | H |
| 23 | H | H | 3-CO(CH₂)₃CH₃ | H |
| 24 | H | H | 4-CO(CH₂)₃CH₃ | H |
| 25 | H | H | 2-CO₂H | H |
| 26 | H | H | 4-CO₂H | H |
| 27 | H | H | 2-CO₂CH₃ | H |
| 28 | H | H | 3-CO₂CH₃ | H |
| 29 | H | H | 4-CO₂CH₃ | H |
| 30 | H | H | 2-CO₂(CH₂)₃CH₃ | H |
| 31 | H | H | 3-CO₂(CH₂)₃CH₃ | H |
| 32 | H | H | 4-CO₂(CH₂)₃CH₃ | H |
| 33 | H | H | 2-COCH₃ | H |
| 34 | H | H | 4-COCH₃ | H |
| 35 | H | H | 2-CO(CH₂)₃CH₃ | H |
| 36 | H | H | 3-CO(CH₂)₃CH₃ | H |
| 37 | H | H | 4-CO(CH₂)₃CH₃ | H |
| 38 | H | H | 2-NH₂ | H |
| 39 | H | H | 3-NH₂ | H |
| 40 | H | H | 4-NH₂ | H |
| 41 | H | H | 2-NHCH₃ | H |
| 42 | H | H | 3-NHCH₃ | H |
| 43 | H | H | 4-NHCH₃ | H |
| 44 | H | H | 2-NH(CH₂)₃CH₃ | H |
| 45 | H | H | 3-NH(CH₂)₃CH₃ | H |
| 46 | H | H | 4-NH(CH₂)₃CH₃ | H |
| 47 | H | H | 2-COCH₂CH₃ | H |
| 48 | H | H | 3-COCH₂CH₃ | H |
| 49 | H | H | 4-COCH₂CH₃ | H |
| 50 | H | H | 2-COCH₂Br | H |
| 51 | H | H | 4-COCH₂Br | H |
| 54 | H | H | 4-COCH₂N₃ | H |
| 55 | H | H | 2-CH₂CHO | H |
| 56 | H | H | 2-(CH₂)₂OH | H |
| 57 | H | H | 3-(CH₂)₂OH | H |
| 58 | H | H | 4-(CH₂)₂OH | H |
| 59 | H | H | 2-CH₂OH | H |
| 60 | H | H | 4-CH₂OH | H |
| 61 | H | H | 2-CH₂NH₂ | H |
| 62 | H | H | 4-CH₂NH₂ | H |
| 63 | H | H | 2-CF₂CHO | H |
| 64 | H | H | 3-CF₂CHO | H |
| 65 | H | H | 4-CF₂CHO | H |
| 66 | H | H | 2-CF₂CH₂OH | H |
| 67 | H | H | 3-CF₂CH₂OH | H |
| 68 | H | H | 4-CF₂CH₂OH | H |
| 69 | H | H | 2-CH₃ | H |
| 70 | H | H | 3-CH₃ | H |
| 71 | H | H | 4-CH₃ | H |
| 72 | H | H | 2-(CH₂)₃CH₃ | H |
| 73 | H | H | 3-(CH₂)₃CH₃ | H |
| 74 | H | H | 4-(CH₂)₃CH₃ | H |
| 75 | H | H | 2-II, R⁴ = CH₃ | H |
| 76 | H | H | 3-II, R⁴ = CH₃ | H |
| 77 | H | H | 4-II, R⁴ = CH₃ | H |
| 78 | H | H | 2-CHO | 3-OH |
| 79 | H | H | 4-CHO | 3-OH |
| 80 | 5-CH₂CH₃ | H | 2-II, R⁴ = H | 3-OH |
| 81 | 5-CH₂CH₂CH₃ | H | 3-II, R⁴ = H | H |
| 82 | H | H | 2-B(OH)₂ | H |
| 83 | H | H | 3-B(OH)₂ | H |
| 84 | H | H | 4-B(OH)₂ | H |
| 85 | H | H | 2-IIA | H |
| 86 | H | H | 3-IIA | H |

TABLE I-continued

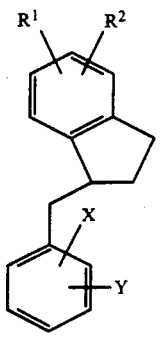

| Ex | R¹ | R² | X | Y |
|---|---|---|---|---|
| 87 | H | H | 4-IIA | H |
| 88 | 5-F | H | 3-CH₂CHO | H |
| 89 | 5-F | H | 4-CH₂CHO | H |
| 90 | 5-F | H | 3-COCH₂Br | H |
| 91 | 5-F | H | 4-COCH₂Br | H |
| 92 | 5-F | H | 3-II, R⁴ = H | H |
| 93 | 5-F | H | 4-II, R⁴ = H | H |
| 94 | 5-F | H | 3-II, R⁴ = CH₃ | H |
| 95 | 5-F | H | 4-II, R⁴ = CH₃ | H |
| 96 | 5-F | H | 3-CHO | 3-OH |
| 97 | 6-F | H | 3-CH₂CHO | H |
| 98 | 6-F | H | 4-CH₂CHO | H |
| 101 | 6-F | H | 3-II, R⁴ = H | H |
| 102 | 6-F | H | 4-II, R⁴ = H | H |
| 103 | 6-F | H | 3-II, R⁴ = CH₃ | H |
| 104 | 6-F | H | 4-II, R⁴ = CH₃ | H |
| 105 | 6-F | H | 3-CHO | 2-OH |
| 106 | 5-CH₃ | H | 3-CH₂CHO | H |
| 107 | 5-CH₃ | H | 4-CH₂CHO | H |
| 108 | 5-CH₃ | H | 3-COCH₂Br | H |
| 109 | 5-CH₃ | H | 4-COCH₂Br | H |
| 110 | 5-CH₃ | H | 3-II, R⁴ = H | H |
| 111 | 5-CH₃ | H | 4-II, R⁴ = H | H |
| 112 | 5-CH₃ | H | 3-II, R⁴ = CH₃ | H |
| 113 | 5-CH₃ | H | 4-II, R⁴ = CH₃ | H |
| 114 | 5-CH₃ | H | 3-CHO | 2-OH |
| 115 | 6-CH₃ | H | 3-CH₂CHO | H |
| 116 | 6-CH₃ | H | 4-CH₂CHO | H |
| 117 | 6-CH₃ | H | 3-COCH₂Br | H |
| 118 | 6-CH₃ | H | 4-COCH₂Br | H |
| 119 | 6-CH₃ | H | 3-II, R⁴ = H | H |
| 120 | 6-CH₃ | H | 4-II, R⁴ = H | H |
| 121 | 6-CH₃ | H | 3-II, R⁴ = CH₃ | H |
| 122 | 6-CH₃ | H | 4-II, R⁴ = CH₃ | H |
| 123 | 6-CH₃ | H | 3-CHO | 2-OH |
| 124 | 5-OCH₃ | H | 3-CH₂CHO | H |
| 125 | 5-OCH₃ | H | 4-CH₂CHO | H |
| 126 | 5-OCH₃ | H | 3-COCH₂Br | H |
| 127 | 5-OCH₃ | H | 4-COCH₂Br | H |
| 128 | 5-OCH₃ | H | 3-II, R⁴ = H | H |
| 129 | 5-OCH₃ | H | 4-II, R⁴ = H | H |
| 130 | 5-OCH₃ | H | 3-II, R⁴ = CH₃ | H |
| 131 | 5-OCH₃ | H | 4-II, R⁴ = CH₃ | H |
| 132 | 6-OCH₃ | H | 3-CH₂CHO | H |
| 133 | 6-OCH₃ | H | 4-CH₂CHO | H |
| 134 | 6-OCH₃ | H | 3-COCH₂Br | H |
| 135 | 6-OCH₃ | H | 4-COCH₂Br | H |
| 136 | 6-OCH₃ | H | 3-II, R⁴ = H | H |
| 137 | 6-OCH₃ | H | 4-II, R⁴ = H | H |
| 138 | 6-OCH₃ | H | 3-II, R⁴ = CH₃ | H |
| 139 | 6-OCH₃ | H | 4-II, R⁴ = CH₃ | H |
| 140 | 5-CO₂CH₃ | H | 3-CH₂CHO | H |
| 141 | 5-CO₂CH₃ | H | 4-CH₂CHO | H |
| 142 | 5-CO₂CH₃ | H | 3-II, R⁴ = H | H |
| 143 | 5-CO₂CH₃ | H | 3-II, R⁴ = H | H |
| 144 | 5-CO₂CH₃ | H | 4-II, R⁴ = H | H |
| 145 | 5-CO₂CH₃ | H | 4-II, R⁴ = CH₃ | H |
| 146 | 5-CO₂CH₃ | H | 3-CHO | 2-OH |
| 147 | 6-CO₂CH₃ | H | 3-CH₂CHO | H |
| 148 | 5-CO₂CH₃ | H | 4-CH₂CHO | H |
| 149 | 6-CO₂CH₃ | H | 3-II, R⁴ = H | H |
| 150 | 6-CO₂CH₃ | H | 4-II, R⁴ = H | H |
| 151 | 6-CO₂CH₃ | H | 3-II, R⁴ = CH₃ | H |
| 152 | 6-CO₂CH₃ | H | 4-II, R⁴ = CH₃ | H |

TABLE I-continued

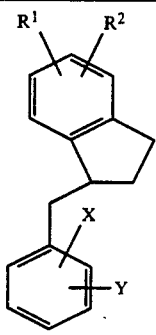

| Ex  | R¹      | R²      | X              | Y    |
|-----|---------|---------|----------------|------|
| 153 | 6-CO₂CH₃ | H       | 3-CHO          | 2-OH |
| 154 | 5-CO₂H  | H       | 3-CH₂CHO       | H    |
| 155 | 5-CO₂H  | H       | 4-CH₂CHO       | H    |
| 156 | 5-CO₂H  | H       | 3-II, R⁴ = H   | H    |
| 157 | 5-CO₂H  | H       | 4-II, R⁴ = H   | H    |
| 158 | 5-CO₂H  | H       | 3-II, R⁴ = CH₃ | H    |
| 159 | 5-CO₂H  | H       | 4-II, R⁴ = CH₃ | H    |
| 160 | 5-CO₂H  | H       | 3-CHO          | H    |
| 161 | 6-CO₂H  | H       | 3-CH₂CHO       | H    |
| 162 | 6-CO₂H  | H       | 4-CH₂CHO       | H    |
| 163 | 6-CO₂H  | H       | 3-II, R⁴ = H   | H    |
| 164 | 6-CO₂H  | H       | 4-II, R⁴ = H   | H    |
| 165 | 6-CO₂H  | H       | 3-II, R⁴ = CH₃ | H    |
| 166 | 6-CO₂H  | H       | 4-II, R⁴ = CH₃ | H    |
| 167 | 6-CO₂H  | H       | 3-CHO          | 2-OH |
| 168 | 6-OCH₃  | 5-CO₂H  | 3-CH₂CHO       | H    |
| 169 | 6-OCH₃  | 5-CO₂H  | 4-CH₂CHO       | H    |
| 170 | 6-OCH₃  | 5-CO₂H  | 3-II, R⁴ = H   | H    |
| 171 | 6-OCH₃  | 5-CO₂H  | 4-II, R⁴ = H   | H    |
| 172 | 6-OCH₃  | 5-CO₂H  | 3-II, R⁴ = CH₃ | H    |
| 173 | 6-OCH₃  | 5-CO₂H  | 4-II, R⁴ = CH₃ | H    |

Dosage and Dosage Forms

The PLA₂ inhibitors of this invention can be administered to treat inflammatory and/or allergic conditions, including but not limited to rheumatoid arthritis and other rheumatic disorders, collagen diseases, allergic diseases, chronic obstructive and bronchospastic lung diseases such as asthma and bronchitis. The compounds of this invention may also be useful in the treatment of osteoarthritis.

They may be administered by any means that enables the active agent to reach the agent's site of action in the body of a mammal. They can be administered by any of the conventional means available for administration of pharmaceuticals, either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration generally contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhalers. Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose) and related sugar solutions, and glycols such as propylene glycol or polyethylene glycols are suitable carriers for parenteral solutions. Solutions for parenteral administration contain the active ingredient, and, if necessary, suitable stabilizing agents, and/or, buffer substances. Antioxidants such as sodium bisulfite, sodium sulfite, or ascorbic acid either alone or in combination are frequently suitable stabilizing agents. Also used are citric acid and its salts and sodium EDTA. In addition, parenteral solutions can contain preservatives, such as benzalkonium chloride, methyl and/or propyl parabens, and chlorobutanol.

Suitable pharmaceutical carriers are described in Remington's Pharamaceutical Sciences, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams of magnesium stearate.

Soft Gelatin Capsules

A mixture of active ingredient in soybean oil is prepared and injected by means of a positive displacement pump into gelatin to form soft gelatin capsules each containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

Injectable

A parenteral composition suitable for administration by injection is prepared by dissolving 1.5% by weight of active ingredient in a solution containing 10% by volume of propylene glycol in water. The solution is sterilized by commonly used techniques.

Suspension ion

An aqueous suspension is prepared for oral administration so that each 5 milliliters contains 25 milligrams of finely divided active ingredient, 200 milligrams of sodium carboxymethyl cellulose, 5 milligrams of sodium benzoate, 1.0 gram of sorbitol solution, U.S.P., and 0.02% milliliters of vanillin.

Nasal Spray

An aqueous solution is prepared such that each 1 milliliter contains 10 milligrams of active ingredient, 1.8 milligrams methylparaben, 0.2 milligram propylparaben and 10 milligrams methylcellulose. The solution is dispensed into 1 milliliter vials.

Lung Inhaler

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

UTILITY SECTION Phospholipase $A_2$ Inhibition Test System

Compounds of this invention have been shown to inhibit phospholipase $A_2$ ($PLA_2$) in an in vitro test system. The $PLA_2$ inhibitors of this invention can be administered to treat inflammatory and/or allergic conditions, including but not limited to rheumatoid arthritis and other rheumatic disorders, collagen diseases, allergic diseases, chronic obstructive and bronchospastic lung diseases such as asthma and bronchitis. The compounds of this invention may also be useful in the treatment of osteoarthritis.

$PLA_2$ from Crotalus adamanteus (1 μg; snake venom) is mixed with 100 mmol liposomal phosphatidylcholine in 50 mM Hepes, 10 mM $CaCl_2$, pH 9.0. The compound is added at various predetermined concentrations to the enzyme solution, and the mixture is then incubated for one hour at 37° C.

The reaction is stopped by the addition of the ethyl acetate and acetic acid (99:1). The released fatty acids (arachidonic acid) are separated from lysophosphatidylcholine and the non-hydrolyzed substrate by washing with ethyl acetate/acetic acid (99:1) through a silica gel chromatography column. The lysophosphatidylcholine and non-metabolized phosphatidylcholine are then eluted using a mixture of ethyl acetate, methanol and water (equal volumes).

The $PLA_2$ enzymatic activity is calculated using the percent of total arachidonic acid product released after subtracting the "zero" control value, then converting the disintegration per minute to mmol of arachidonic acid products released.

The $IC_{50}$ value of a compound is determined by inspection of a semilog plot of inhibition versus final inhibitor concentrations.

The enzyme PLA2 catalyzes the release of fatty acids from the 2-position of phospholipids, particularly phosphatidylcholine. Arachidonic acid (AA) is most frequently found at the 2-position of phospholipids. Once it is released by the action of $PLA_2$, AA can be oxygenated by cyclooxygenases and lipoxygenases to the potent inflammatory mediators, prostaglandins and leukotrienes, respectively. Inhibition of $PLA_2$ will block the generation of these local inflammatory mediators, thereby reducing inflammation. Since AA is the substrate for both cyclooxygenases and lipoxygenases, inhibition of $PLA_2$ will reduce the levels of both prostaglandins and leukotrienes. Many current anti-inflammatory drugs, e.g., salicylates, inhibit cyclooxygenases but not lipoxygenases, so that only prostaglandin levels are reduced.

Carrageenan Paw Edema Assay

The compounds of formula (I) have been shown to be efficacious in murine models of skin inflammatory diseases. One such model is the inflammations induced by lambda carrageenan, by the method of Winter et al., *Proc. Soc. Exo. Biol Med,* 1962, 111, 544–547. This model mimics many of the inflammatory changes which occur in human skin diseases such as psoriasis. The test procedure is as follows: male Caesarian-derived Sprague-Dawley rates from Charles River Laboratories are maintained on rat chow and water ad libidum and on a 12 hour light/12 hour dark cycle until they weight 160–210 grams.

All compounds including standards are suspended in sterile 0.25% methylcellulose (Type A 15C, viscosity 1500 c.p.s. at 2%; Dow Chemical Company). One drop of Tween 80 per 10 ml of methylcellulose and 4 mm glass beads are added to each suspension. Each compound is bead-milled for one hour prior to use.

Groups of 10 rats per treatment regimen are dosed with vehicle only, standards or appropriate compounds at 1 ml/100 grams body weight for doses at 50 mg/kg over a 24-hour period before carrageenan. Dosing is intraperitioneal.

After dosing, all animals are given tap water so that the total volumes of fluid administered to each rat orally is 5.0 ml. This achieves uniform hydration of the rats and thus minimizes variability of the edematous response in the paw.

Sigma Type IV lambda carrageenan (Sigma Chemical Company, St. Louis, Mo., #C3889) is suspended in 0.9% sterile saline usually as a 1% solution (100 mg/10 ml). This preparation is bead-milled one hour prior to use.

One hour after dosing the standards or compounds, the control and experimental groups are injected subcutaneously in the plantar region of the left rear paw. The negative control is injected with 0.1 ml of 0.9% sterile saline and the positive control with 0.1 ml of 1% carrageenan. All drug-treated groups receive the carrageenan injection. All injections are done using a 23 gauge needle.

Immediately following injection initial paw volume readings are taken, and then again three hours later using a Ugo Basile volume plethysmometer. The differences between the initial reading and the three hour reading is then calculated. Means; S.E.M. of these difference are determined for each group. The percent decrease from the control volumes are calculated using the following formula:

% Inhibition = $\left[1 - \frac{(\text{Experimental} - \text{Negative Control})}{(\text{Positive Control} - \text{Negative Control})}\right]$ 100.

Data are evaluated using the Student's t-test and p 0.05 is considered significant.

TABLE 2

Enzymatic PLA$_2$ Inhibition and Carrageenan Paw Edema Assay

| Compound | Snake Venom PLA$_2$ (IC50) | Carr. Paw Edemia Inhib. % |
|---|---|---|
| Ex. 12 | 2.4 μM | 51% (n = 3) |
| Ex. 16 | 2.6 μM | 42% (n = 3) |
| 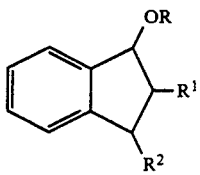 | Inactive at 1 mM | −4% (n = 1) |

What is claimed is:

1. A compound of formula I

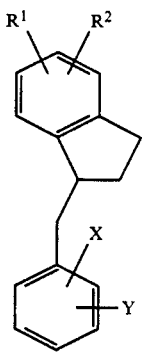   I or a pharmaceutically acceptable salt thereof, wherein:

R$^1$ is H, halo, alkyl of 1-4 carbon atoms, OR$^3$ or CO$_2$R$^4$;

R$^2$ is H or when R$^1$ is 6—OR$^3$, then R$^2$ may be 5—CO$_2$R$^4$;

X is COR$^3$, CO$_2$R$^4$, CN, NHR$^4$, COCH$_2$R$^5$, CHO, CH$_2$CHO, CH$_2$NH$_2$, CF$_2$CHO, COCF$_3$, C$_1$-C$_4$ alkyl, halo,

   (II)

Y is H, or when X is —CHO, then Y may be ortho —OH relative to —CHO;

R$^3$ is alkyl of 1-4 carbon atoms;

R$^4$ is H or alkyl of 1-4 carbon atoms; and

R$^5$ is Cl, Br, or N$_3$; provided that:

(a) when X is COCH$_2$R$^5$, then neither R$^1$ nor R$^2$ is CO$_2$H;

(b) when R$^1$ is OR$^3$, then X is not OR$^3$;

(c) when X is CHO and Y is OH, then R$^1$ is not OR$^3$;

(d) neither R$^1$ nor R$^2$, except when H, resides at the 7-position;

(e) when X is CF$_2$CHO then neither R$^1$ nor R$^2$ is CO$_2$R$^4$;

(f) when R$^1$ is 6—OR$^3$ and R$^2$ is 5—CO$_2$R$^4$, then X is CH$_2$CHO, or

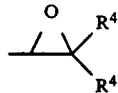

(g) when R$^1$ or R$^2$ is CO$_2$R$^4$ and X is CO$_2$R$^4$, then R$^4$ is the same in R$^1$ or R$^2$ and in X.

2. The compound of claim 1, wherein:

R$^1$ and R$^2$ are H;

X is COR$^3$, CO$_2$R$^4$, COCH$_2$R$^5$, CN, CHO, CH$_2$CHO, or

Y is H, but if X is CHO then Y may be OH ortho to CHO;

R$^3$ is alkyl of 1-4 carbons;

R$^4$ is H, alkyl of 1-4 carbons; and

R$^5$ is Cl, Br, N$_3$.

3. The compound of claim 2 wherein

X is COCH$_2$Br, CH$_2$CHO, CHO or

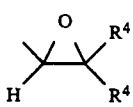

and

Y is H, and if X is CHO, then Y may be OH ortho to CHO.

4. The compound of claim 1 which is 3-(2′,3′-dihydroinden-1′-ylmethyl)-alpha-bromoacetophenone.

5. The compound of claim 1 which is 3-(2′,3′-dihydroinden-1′-ylmethyl)-orixanylbenzene.

6. The compound of claim 1 which is 4-(2′,3′-dihydroinden-1′-ylmethyl)-oxiranylbenzene.

7. The compound of claim 1 which is 4-(2′,3′-dihydroinden-1′-ylmethyl)-phenylacetaldehyde.

8. The compound of claim 1 which is 3-(2′,3′-dihydroinden-1′-ylmethyl)-phenylacetaldehyde.

9. The compound of claim 1 which is 3-(2′,3′-dihydroinden-1′-ylmethyl)-2-hydroxybenzaldehyde.

10. A pharmaceutical composition comprising a pharmaceutically acceptable carrier and a pharmaceutically effective anti-inflammatory and/or anti-allergic amount of a compound of claim 1.

11. A pharmaceutical composition comprising a pharmaceutically acceptable carrier and a pharmaceutically effective anti-inflammatory and/or anti-allergic amount of a compound of claim 2.

12. A pharmaceutical composition comprising a pharmaceutically acceptable carrier and a pharmaceutically effective anti-inflammatory and/or anti-allergic amount of a compound of claim 3.

13. A pharmaceutical composition comprising a pharmaceutically acceptable carrier and a pharmaceutically effective anti-inflammatory and/or anti-allergic amount of the compound of claim 4.

14. A pharmaceutical composition comprising a pharmaceutically acceptable carrier and a pharmaceutically effective anti-inflammatory and/or anti-allergic amount of the compound of claim 5.

15. A pharmaceutical composition comprising a pharmaceutically acceptable carrier and a pharmaceutically effective anti-inflammatory and/or anti-allergic amount of the compound of claim 6.

16. A pharmaceutical composition comprising a pharmaceutically acceptable carrier and a pharmaceutically effective anti-inflammatory and/or anti-allergic amount of the compound of claim 7.

17. A pharmaceutical composition comprising a pharmaceutically acceptable carrier and a pharmaceutically effective anti-inflammatory and/or anti-allergic amount of the compound of claim 8.

18. A pharmaceutical composition comprising a pharmaceutically acceptable carrier and a pharmaceutically effective anti-inflammatory and/or anti-allergic amount of the compound of claim 9.

19. A method of treating inflammatory and/or allergic conditions in a mammal comprising administering to a mammal in need of such treatment a therapeutically effective amount of a compound of claim 1.

20. A method of treating inflammatory and/or allergic conditions in a mammal comprising administering to a mammal in need of such treatment a therapeutically effective amount of a compound of claim 2.

21. A method of treating inflammatory and/or allergic conditions in a mammal comprising administering to a mammal in need of such treatment a therapeutically effective amount of a compound of claim 3.

22. A method of treating inflammatory and/or allergic conditions in a mammal comprising administering to a mammal in need of such treatment a therapeutically effective amount of a compound of claim 4.

23. A method of treating inflammatory and/or allergic conditions in a mammal comprising administering to a mammal in need of such treatment a therapeutically effective amount of a compound of claim 5.

24. A method of treating inflammatory and/or allergic conditions in a mammal comprising administering to a mammal in need of such treatment a therapeutically effective amount of a compound of claim 6.

25. A method of treating inflammatory and/or allergic conditions in a mammal comprising administering to a mammal in need of such treatment a therapeutically effective amount of a compound of claim 7.

26. A method of treating inflammatory and/or allergic conditions in a mammal comprising administering to a mammal in need of such treatment a therapeutically effective amount of a compound of claim 8.

27. A method of treating inflammatory and/or allergic conditions in a mammal comprising administering to a mammal in need of such treatment a therapeutically effective amount of a compound of claim 9.

* * * * *